United States Patent
Butler et al.

(10) Patent No.: US 6,758,854 B1
(45) Date of Patent: *Jul. 6, 2004

(54) SPLITTABLE OCCLUSION BALLOON SHEATH AND PROCESS OF USE

(75) Inventors: William Butler, Minneapolis, MN (US); John Ockuly, Robbinsdale, MN (US); Joseph J. Florio, Lacanada, CA (US); Gene A. Bornzin, Simi Valley, CA (US); Steven E. Scott, Excelsior, MN (US)

(73) Assignees: St. Jude Medical; Daig Division, Inc., Minnetonka, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/344,535

(22) Filed: Jun. 25, 1999

Related U.S. Application Data

(63) Continuation-in-part of application No. 09/207,295, filed on Dec. 8, 1998, now Pat. No. 6,083,207, and a continuation-in-part of application No. 08/853,631, filed on May 9, 1997, now Pat. No. 6,277,107.

(51) Int. Cl.$^7$ .............................................. A61B 29/00
(52) U.S. Cl. .................................. 606/194; 604/101.01
(58) Field of Search ............................... 606/192, 194, 606/195, 198, 108; 604/103.1, 103.14, 101.01, 104, 101.02–101.05, 96.01, 99.02, 103.05–103.07, 917, 918–920

(56) References Cited

U.S. PATENT DOCUMENTS

| | | |
|---|---|---|
| 2,024,982 A | 12/1935 | Scott et al. |
| 4,161,177 A | 7/1979 | Fuchs |
| 4,166,469 A | 9/1979 | Littleford |
| 4,243,050 A | 1/1981 | Littleford |
| 4,323,071 A | 4/1982 | Simpson et al. |
| 4,345,606 A | 8/1982 | Littleford |
| 4,451,256 A | 5/1984 | Weikl et al. |
| RE31,855 E | 3/1985 | Osborne |
| 4,569,347 A | 2/1986 | Frisbie |
| 4,581,025 A | 4/1986 | Timmermans |
| 4,648,384 A | 3/1987 | Schmukler |
| 4,747,833 A | 5/1988 | Kousai et al. ............. 604/164 |
| 4,748,982 A * | 6/1988 | Horzewski et al. |
| 4,772,266 A | 9/1988 | Groshong .................. 604/164 |
| 4,819,751 A | 4/1989 | Shimada et al. |

(List continued on next page.)

FOREIGN PATENT DOCUMENTS

| WO | WO 00/20054 | 10/1996 |
|---|---|---|
| WO | WO 98/39040 | 9/1998 |

* cited by examiner

*Primary Examiner*—Michael J. Milano
*Assistant Examiner*—(Jackie) Tan-Uyen T. Ho
(74) *Attorney, Agent, or Firm*—Heimbecher & Assoc., LLC; Reed R. Heimbecher

(57) ABSTRACT

A splittable occlusion balloon sheath includes a splittable sheath onto which an occlusion balloon has been secured near the distal end of the splittable sheath. A splittable hemostasis valve or a partitioned hemostasis valve system may also be secured within or to the splittable occlusion balloon sheath. This splittable occlusion balloon sheath is utilized to introduce a medical device, such as electrode leads, into the coronary sinus of the human heart. A dilator may also be used with the splittable occlusion balloon sheath for introduction of the medical devices. The splittable occlusion balloon sheath and/or the dilator may be precurved with a particular shape to assist in the introduction of the splittable occlusion balloon sheath and/or dilator into the coronary sinus. Also disclosed is a process of use of the splittable occlusion balloon system within the coronary sinus.

35 Claims, 21 Drawing Sheets

U.S. PATENT DOCUMENTS

| | | | |
|---|---|---|---|
| 4,921,479 A | 5/1990 | Grayzel | 604/53 |
| 4,927,412 A | 5/1990 | Menasche | |
| 4,960,412 A | 10/1990 | Fink | 604/167 |
| 4,983,168 A | 1/1991 | Moorehead | |
| 5,098,392 A | 3/1992 | Fleischhacker | |
| 5,125,904 A | 6/1992 | Lee | |
| 5,129,394 A | 7/1992 | Mehra | |
| 5,171,232 A | 12/1992 | Castillo et al. | |
| 5,203,776 A | 4/1993 | Durfee | |
| 5,221,258 A | 6/1993 | Shturman | |
| 5,267,958 A * | 12/1993 | Buchbinder et al. | 604/103.14 |
| 5,312,355 A | 5/1994 | Lee | |
| 5,322,509 A | 6/1994 | Rickerd | |
| 5,397,311 A | 3/1995 | Walker et al. | |
| 5,413,559 A * | 5/1995 | Sirhan et al. | 604/103.1 |
| 5,423,772 A | 6/1995 | Lurie et al. | |
| 5,441,504 A | 8/1995 | Pohndorf et al. | |
| 5,488,960 A | 2/1996 | Toner | |
| 5,509,908 A | 4/1996 | Hillstead et al. | |
| 5,536,250 A | 7/1996 | Klein et al. | 604/96 |
| 5,549,555 A * | 8/1996 | Sohn | 604/101 |
| 5,549,581 A | 8/1996 | Lurie et al. | |
| 5,571,161 A | 11/1996 | Starksen | |
| 5,613,953 A | 3/1997 | Pohndorf | |
| 5,643,321 A | 7/1997 | McDevitt | |
| 5,669,383 A | 9/1997 | Johnson | |
| 5,720,726 A | 2/1998 | Marcadis et al. | |
| 5,722,963 A | 3/1998 | Lurie et al. | |
| 5,755,693 A | 5/1998 | Walker et al. | |
| 5,755,702 A | 5/1998 | Hillstead et al. | |
| 5,807,326 A | 9/1998 | O'Neill et al. | |
| 5,814,016 A | 9/1998 | Valley et al. | |
| 5,814,029 A | 9/1998 | Hassett | |
| 5,873,858 A | 2/1999 | Schafer et al. | 604/161 |
| 5,928,163 A | 7/1999 | Robert et al. | |
| 6,375,648 B1 | 4/2002 | Edelman et al. | |

(List continued on next page.)

SUPERIOR APPROACH

1 FOSSA OVALIS
2 SPLITTABLE OCCLUSION BALLOON SHEATH
3 INFERIOR VENA CAVA
4 OS OF CORONARY SINUS
5 CORONARY SINUS
6 EUSTATION RIDGE
7 SUPERIOR VENA CAVA
8 OCCLUSION BALLOON

INFERIOR APPROACH

1. FOSSA OVALIS
2. SPLITTABLE OCCLUSION BALLOON SHEATH
3. INFERIOR VENA CAVA
4. OS OF CORONARY SINUS
5. CORONARY SINUS
6. EUSTATION RIDGE
7. SUPERIOR VENA CAVA
8. OCCLUSION BALLOON

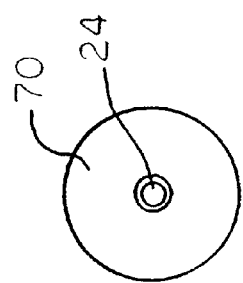
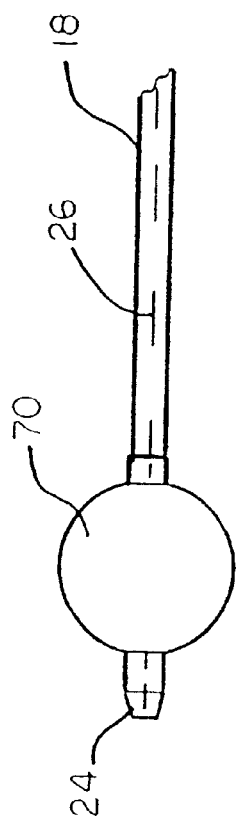
FIG. 10B
FIG. 10A

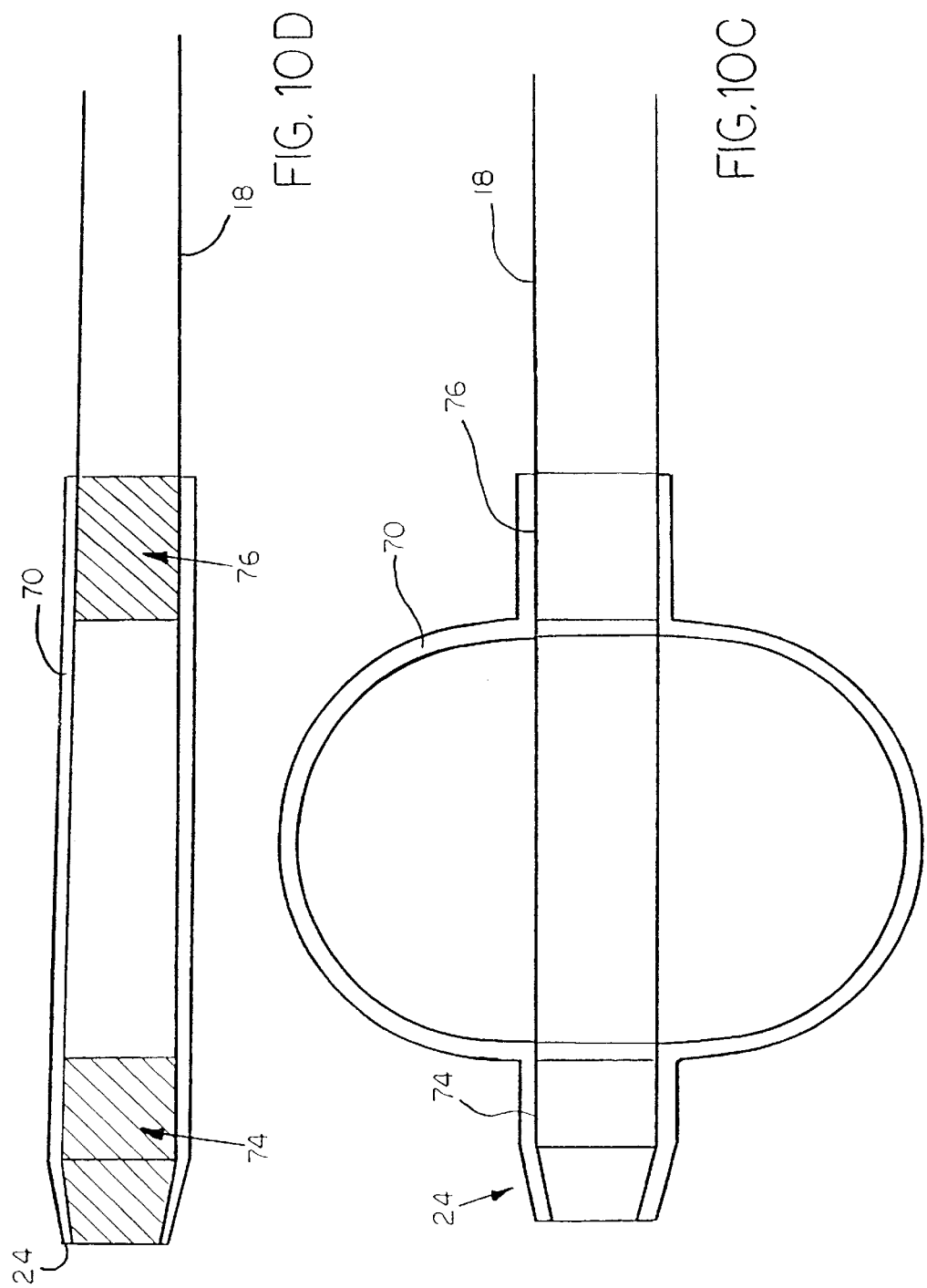

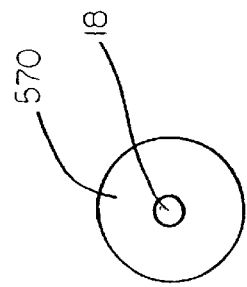
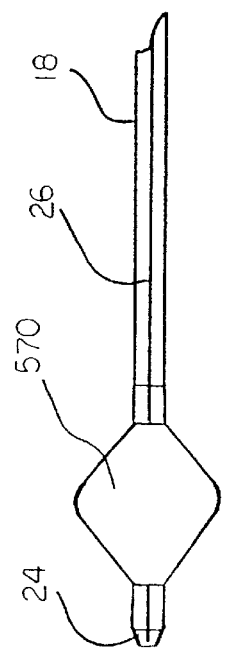

SPLITTABLE OCCLUSION BALLOON SHEATH AND PROCESS OF USE

CROSS-REFERENCE TO RELATED APPLICATIONS

This application is a continuation-in-part application of Ser. No. 08/853,631, filed May 9, 1997 now patent No. 6,277,107, and a continuation-in-part application of Ser. No. 09/207,295 filed Dec. 8, 1998 now U.S. Pat. No. 6,083,207.

BACKGROUND OF INVENTION

1. Field of the Invention

This invention relates to sheaths and introducers which are utilized in the human heart. More particularly this invention relates to a splittable sheath onto which an occlusion balloon has been secured which is utilized for the introduction of specialized medical devices into the vasculature of the heart and a process for the introduction of those devices into the vasculature of the heart utilizing the splittable occlusion balloon sheath.

2. Description of Related Art

Many medical procedures require the introduction of specialized medical devices into the human heart. For example, electrical leads, such as pacemaker leads, defibrillation leads, or leads used for cardioversion, and shunts or specialized catheters are frequently placed at specific locations in the vasculature of the heart to perform specialized cardiac procedures. Many of these medical devices, such as pacemaker leads, are very pliant and flexible. This flexibility is necessary to prevent damage, particularly to the patient's vasculature, during the period of time those devices are present in the patient. However, because of this flexibility, it is quite difficult to advance these devices through the patient's vasculature into the heart without the use of some stiffening element with the device. For example, one method of stiffening these medical devices is to introduce a stylet into the lumen of the medical device.

The typical procedure for introducing these devices into the heart requires passage through the patient's vasculature. One early method of introducing such medical devices into the vasculature was to surgically cut an opening into the patient's vasculature. However, there were several disadvantages to this procedure. To address these disadvantages, percutaneous methods have been developed to create openings in the vasculature. Once an opening is created, frequently by use of a hollow needle, a dilator is usually inserted into the vasculature which gradually increases the size of the opening. The dilator has a tapered end which spreads apart the tissue at the puncture sight as it is advanced through the vasculature. Often the dilator contains a lumen through which other medical devices may be inserted into the vasculature.

In a typical procedure for introduction of an electrode lead into the heart, a guidewire is first introduced through the vasculature into the appropriate chamber of the heart. This process is disclosed, for example, in U.S. Pat. No. 5,488,960. With the guidewire in place, a catheter/sheath or dilator/sheath combination is then passed over the guidewire and directed into the patient's body. The catheter or dilator is then removed from the sheath. The sheath then provides a platform from which the lead may be introduced into the heart, frequently with a stylet placed within the lumen of the lead to assist in stiffening the structure of the lead and also to permit precise placement of the device within the heart.

With conventional introducers or sheaths, the maximum diameter of the pacemaker lead that can be inserted is no larger than the size of the lumen of the sheath. This limitation created a significant problem because of the nature of pacemaker leads. Frequently, the proximal end of the pacemaker lead contains an electrical connector for connection to a pulse generator. Because the size of the connecter is often larger than the diameter of the lumen of conventional cardiac introducers, splittable sheaths have been designed to assist in the insertion of these electrode leads. See, for example, U.S. Pat. Nos. 5,098,392, 4,983,168, 4,581,025, 4,451,256, 4,345,606, 4,243,050, 4,166,469 and Re 31,855. Once the splittable sheath directs the placement of the medical device, such as an electrode lead, into the correct location within the human body, it is torn apart lengthwise as it is withdrawn from the body. By being splittable, the size of the lumen of the splittable sheath can remain relatively small as it need be no larger than is necessary for passage of the distal tip of the medical device through the lumen of the sheath.

Even with these smaller diameter splittable sheaths, a problem has developed during their use. During introduction of a pacemaker lead, a significant amount of bleeding may occur at the operation site, depending upon the blood pressure present in the vessel. Once the sheath is in place within a vessel, the lumen of the sheath can provide a passageway for the free flow of blood away from the operation site. Further, because of this flow of blood, clotting may occur if the sheath remains in position for an extended period of time. These clots may cause emboli which may pass to the lung and have a detrimental impact on the patient. Splittable sheaths may also provide a passageway for the introduction of air into the heart. The inadvertent introduction of air into the blood system can cause air emboli in the patient which may also have negative effects.

Because of these problems these splittable sheaths are removed from the theater of operation as soon as possible, even if it would be preferable to maintain them in position for a longer period of time. Such hurried procedures can result in medical complications.

One method of preventing, or at least limiting, the flow of blood out of a sheath while a pacemaker lead is being introduced is for the physician to place his thumb over the exposed end of the sheath or to squeeze or pinch the exposed end of the sheath between his thumb and forefinger. However, neither of these methods for reducing the undesired flow of blood and air through the sheath is desirable, because the opportunity for loss of blood and introduction of air is still present.

Another solution to this problem is the use of a hemostasis valve secured in a splittable sheath to limit blood flow during the introduction of pacemaker leads into the heart and other similar medical procedures. However, because the exterior end of pacemaker leads is generally larger than the opening in conventional hemostasis valves, it is not possible for the pacemaker leads to pass through those conventional hemostasis valves. Accordingly, splittable hemostasis valves have been secured within splittable sheaths for the introduction of pacemaker leads, for example, in U.S. Pat. Nos. 5,755,693, 5,613,953, 5,441,504, 5,397,311, 5,312,355, and 5,125,904.

However, these valves often are difficult to split when used in a medical procedure because of the presence of fluids, particularly blood. In addition, when these valves are split, blood splattering often occurs. Further, the valve often tears unevenly, making it more difficult to remove the splittable sheath and the splittable valve from the operating theater. Further, some physicians are hesitant to force the tines of leads for pacemakers through these valves because they fear damage to the tines. In addition, some physicians may want to delay the introduction of a hemostasis valve into the sheath even after the sheath is already in position within the patient. To solve these problems, an improved partitioned hemostasis valve system can be utilized, which is disclosed in Ser. No. 09/207,295, filed Dec. 8, 1998 and owned by the assignee, the contents of which are incorporated herein by reference.

Many specialized medical devices are utilized in the vasculature of the heart, specifically in the coronary sinus. The coronary sinus is the largest cardiac vein in the heart and serves as a venous conduit from smaller veins within the myocardium to the right atrium. A tissue fold or primitive valve covers the coronary sinus ostium to prevent blood from backflowing into the coronary sinus as it is being pumped out of the right atrium. Located within the right atrium, generally, above the coronary sinus is an oval depression called the fossa ovalis. Between the inferior vena cava and the coronary sinus ostium is the eustaclan ridge. The location of each of these elements may vary from patient to patient.

The coronary sinus is often used for electrophysiological procedures in the heart, including both diagnostic and treatment procedures. The coronary sinus can also be used for pacing both the left and right sides of the heart. Gaining access to the ostium of the coronary sinus, however, is often a difficult procedure, especially because of the large number of similar anatomical structures located near the coronary sinus within the right atrium. It is especially difficult because these anatomical structures do not show up on a fluoroscope.

Current medical procedures available for introduction of devices such as pacemakers, implantable defibrillators, specialized catheters or devices used for cardioversion or cardioplegia into the coronary sinus are frequently time consuming and difficult. To address these concerns, particular types of diagnostic catheters have been designed as disclosed in U.S. Pat. Nos. 5,423,772, 5,549,581, 5,643,321, and 5,722,963. These patents disclose precurved, coronary sinus catheters, which because of their unique curvature, can be advanced through the patient's vasculature directly into the coronary sinus, where it can be used to perform diagnostic and treatment procedures. U.S. Pat. No. 5,488,960 discloses a different type of device designed for use in the coronary sinus.

One common medical procedure that utilizes a medical device introduced within the coronary sinus is cardioplegia. This procedure is commonly used during heart surgery, and requires the introduction of a cardioplegia solution into the coronary sinus. While numerous cardioplegia catheters have been designed, it has been discovered that medical devices introduced in the coronary sinus can be easily ejected because the coronary sinus walls are slippery, extensible, and tapered so that the coronary sinus vessel becomes smaller in the direction in which the medical device is advanced into the coronary sinus vessel. In order to overcome these problems, occlusion balloons have commonly been secured near the distal end of the cardioplegia catheter. To prevent dislodgement of these occlusion balloon catheters after introduction into the coronary sinus, the outside surface of the occlusion balloon is coated or modified with physical extensions which frictionally engage the coronary sinus and thus provide a higher retentive force for the medical device in the coronary sinus than is present in conventional occlusion balloon surfaces. Typical devices that can be used for this type of medical procedure are disclosed in U.S. Pat. Nos. 4,648,384, 4,927,412, 5,129,394, 5,720,726, and 5,807,326. In addition to the occlusion of the coronary sinus, U.S. Pat. No. 5,814,016 discloses medical devices for occlusion of other vasculature associated with the heart, particularly the aorta, utilizing either concentric or eccentric-shaped occlusion balloons.

While these occlusion balloons secured to conventional cannula have been useful for cardioplegia and certain other types of coronary procedures, there is still a need for devices which assist in the placement of pacemaker electrodes in the coronary sinus. Further, once these pacemaker electrodes are in place, methods must be utilized to remove the supporting medical devices from the heart without dislodging the electrode leads.

Accordingly, it is an aspect of this invention to disclose a device which assists in the efficient placement of medical devices, particularly small, flexible medical devices, such as electrode leads, into the coronary sinus.

It is a still further aspect of the invention to disclose a splittable sheath on which an occlusion balloon has been secured, which assists in the introduction of medical devices into the coronary sinus.

It is a still further aspect of this invention to disclose a fixed shape splittable sheath onto which an occlusion balloon has been secured to assist in the introduction of medical devices into the coronary sinus.

It is another aspect of the invention to disclose a fixed shape splittable occlusion balloon sheath that can be utilized with a fixed shape dilator for placement of small, medical devices into the coronary sinus.

It is a still further aspect of the invention to disclose a splittable occlusion balloon sheath which contains a splittable hemostasis valve, preferably a partitioned hemostasis valve system for introduction of medical devices into the coronary sinus.

It is a still further aspect of the invention to disclose a splittable occlusion balloon sheath for introduction of small medical devices into the coronary sinus, wherein the balloon is constructed such that the distal tip of the occlusion sheath is centered within the coronary sinus when the occlusion balloon is inflated.

It is a still further aspect of the invention to disclose a splittable occlusion balloon sheath for introduction of small medical devices into the coronary sinus, wherein the occlusion balloon contains a system to enhance frictional contact of the occlusion balloon with the coronary sinus to assist in its retention within the coronary sinus throughout the medical procedure.

These and other aspects of the invention are obtained from the various designs of the device of the present invention, and by the processes disclosed herein.

SUMMARY OF INVENTION

The present invention relates to a splittable occlusion balloon sheath comprising an occlusion balloon secured near a distal end of a splittable sheath, utilized to introduce a medical device, such as a pacemaker lead, defibrillator lead, or diagnostic or treatment device, into the coronary sinus of the heart. After utilization, this splittable occlusion balloon sheath can be split into two (2) separate sections, and removed from the operating theater.

The present invention also relates to a splittable occlusion balloon sheath with a predetermined shape, which assists in its placement into the coronary sinus.

The present invention also relates to a splittable occlusion balloon sheath, which contains a hemostasis valve within a lumen of the splittable occlusion balloon sheath, to prevent the backflow of blood through the sheath during a medical procedure. Preferably, the hemostasis valve is also splittable. More preferably, the hemostasis valve is contained within a partitioned hemostasis valve system and includes an adaptor for securing the system to the splittable occlusion balloon sheath.

The invention also encompasses a splittable occlusion balloon sheath system for the introduction of medical devices into the coronary sinus of the human heart, which includes a splittable occlusion balloon sheath and a dilator advanced through a lumen of the sheath. Preferably, the dilator and/or the splittable sheath are formed in predetermined, precurved shapes.

The splittable occlusion balloon sheath is not limited to introducing leads into the coronary sinus. The invention also encompasses a splittable occlusion balloon sheath useful for introducing other small medical devices into the vasculature of the heart, such as electrophysiological diagnostic devices and devices useful for sensing and ablation procedures.

BRIEF DESCRIPTION OF THE DRAWINGS

FIG. 4b is a side view of the splittable occlusion balloon of FIG. 4a rotated 90 degrees from the position of FIG. 4a.

FIG. 6a is a side view of a precurved dilator for use with the splittable occlusion balloon sheath.

FIG. 6b is a side view of the precurved dilator of FIG. 6a rotated 90 degrees from its position in FIG. 6a.

FIG. 6c is an end view of the dilator of FIG. 6a, viewed from its distal end.

FIG. 7b is a side view of the splittable occlusion balloon sheath of FIG. 7a rotated 90 degrees from the position of FIG. 7a.

FIG. 8a is a side view of a precurved dilator for use with the splittable occlusion balloon sheath of FIG. 7a specifically designed for an inferior approach to the coronary sinus.

FIG. 8b is a side view of the precurved dilator of FIG. 8a rotated 90 degrees from its position in FIG. 8a.

FIG. 8c is an end view of the dilator of FIG. 8a viewed from its distal end.

FIG. 10a is a side cutaway view of the distal portion of the splittable occlusion balloon sheath showing the occlusion balloon inflated, wherein the balloon is a circumferential, concentric, spherical, occlusion balloon.

FIG. 10b is a front view of the splittable occlusion balloon sheath of FIG. 10a.

FIG. 10c is a detailed view of the distal end of the splittable occlusion balloon sheath of FIG. 10a, showing one method of securing the occlusion balloon to the sheath with the balloon inflated.

FIG. 10d is the splittable occlusion balloon sheath of FIG. 10c with the balloon not inflated.

FIG. 12a is a side cutaway view of the distal portion of the splittable occlusion balloon sheath showing the use of two (2) side-mounted occlusion balloons.

FIG. 12b is a top view of the splittable occlusion balloon sheath of FIG. 12a.

FIG. 12c is a bottom view of the splittable occlusion balloon sheath of FIG. 12a.

FIG. 12d is a front end view of the splittable occlusion balloon sheath of FIG. 12a.

FIG. 13b is a top view of the splittable occlusion balloon sheath of FIG. 13a.

FIG. 13c is a bottom view of the splittable occlusion balloon sheath of FIG. 13a.

FIG. 13d is a front end view of the splittable occlusion balloon sheath of FIG. 13a.

FIG. 14b is a top view of the splittable occlusion balloon sheath of FIG. 14a.

FIG. 14c is a bottom view of the splittable occlusion balloon sheath of FIG. 14a.

FIG. 14d is a front view of the splittable occlusion balloon sheath of FIG. 14a.

FIG. 15b is an end view of the splittable occlusion balloon sheath of FIG. 15a.

FIG. 16a is a side cutaway view of the distal portion of the splittable occlusion balloon sheath showing the use of a single, circumferential, concentric, conical occlusion balloon.

FIG. 16b is an end view of the splittable occlusion balloon sheath of FIG. 16a.

FIG. 17b is an end view of the splittable occlusion balloon sheath of FIG. 17a.

DETAILED DESCRIPTION OF THE DRAWINGS

Figure 1A:
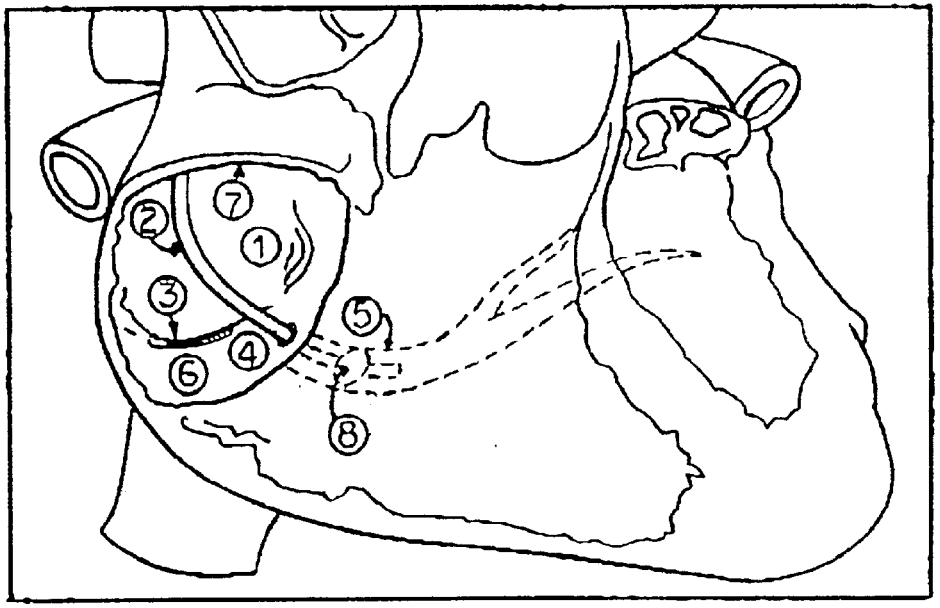
FIG. 1a is a cutaway view of the human heart from the right side showing the splittable occlusion balloon sheath introduced into the coronary sinus using a superior approach.
Figure 1B:
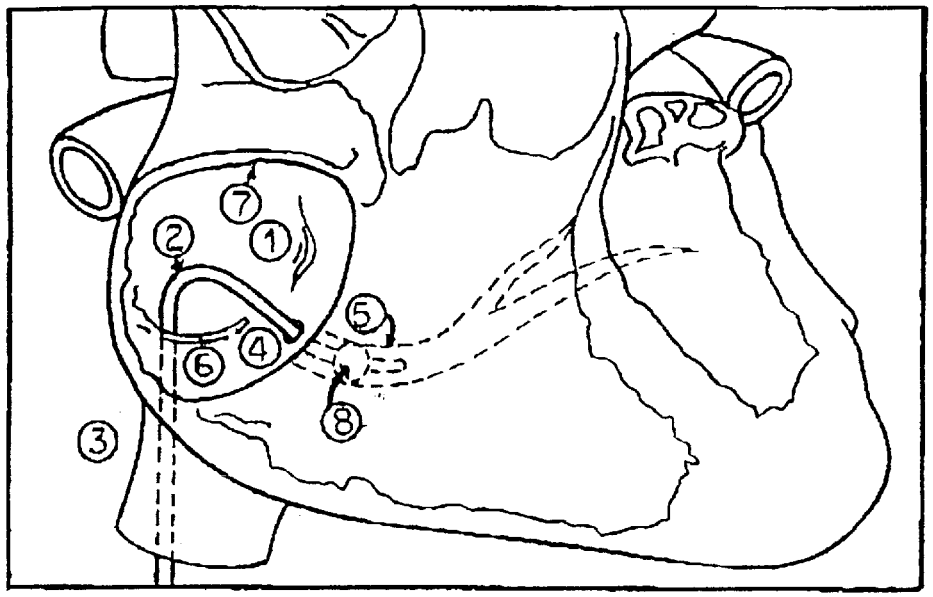
FIG. 1b is a cutaway view of the human heart showing an alternate preferred embodiment of the splittable occlusion balloon sheath within the coronary sinus using an inferior approach.
Figure 2:
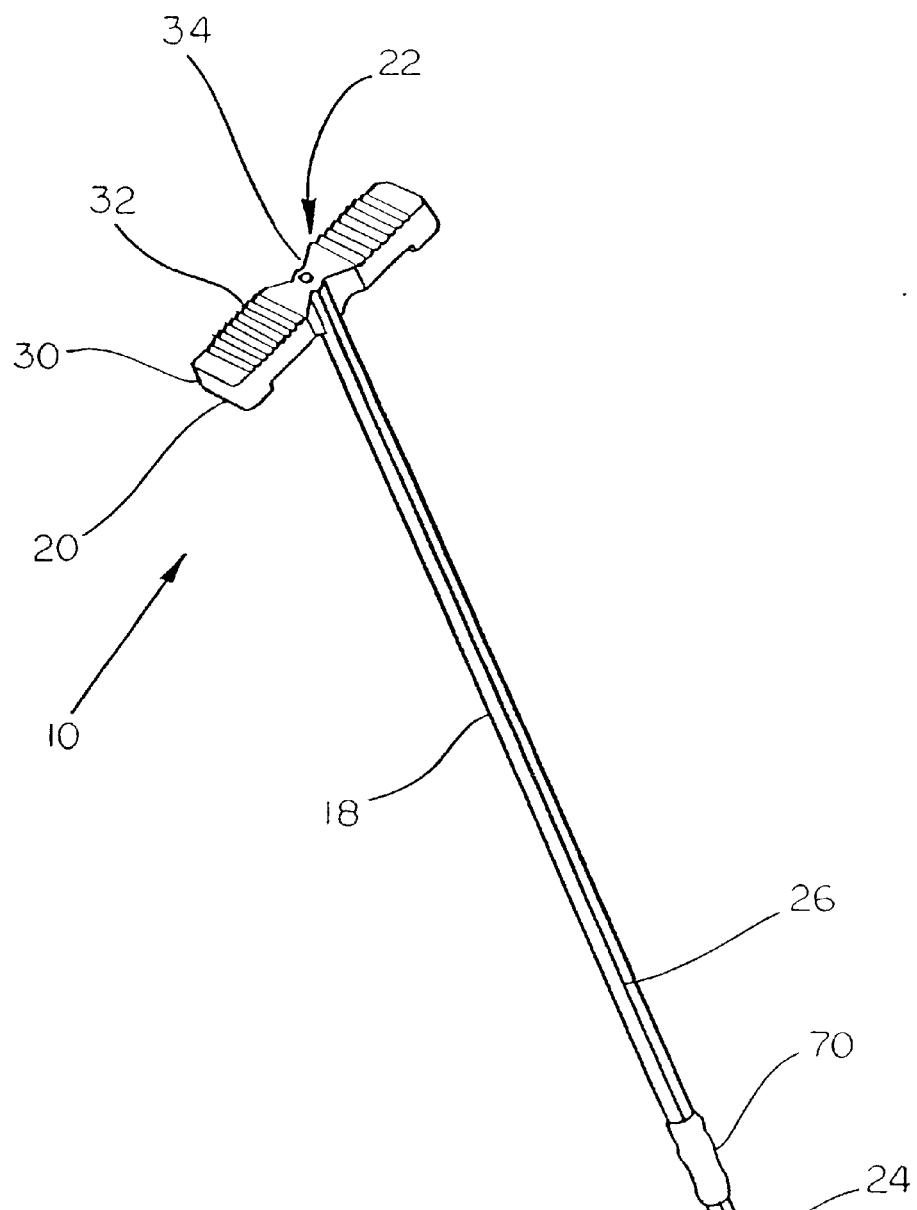
FIG. 2 is a perspective view of a first embodiment of a splittable occlusion balloon sheath with the balloon not inflated.
Figure 2A:
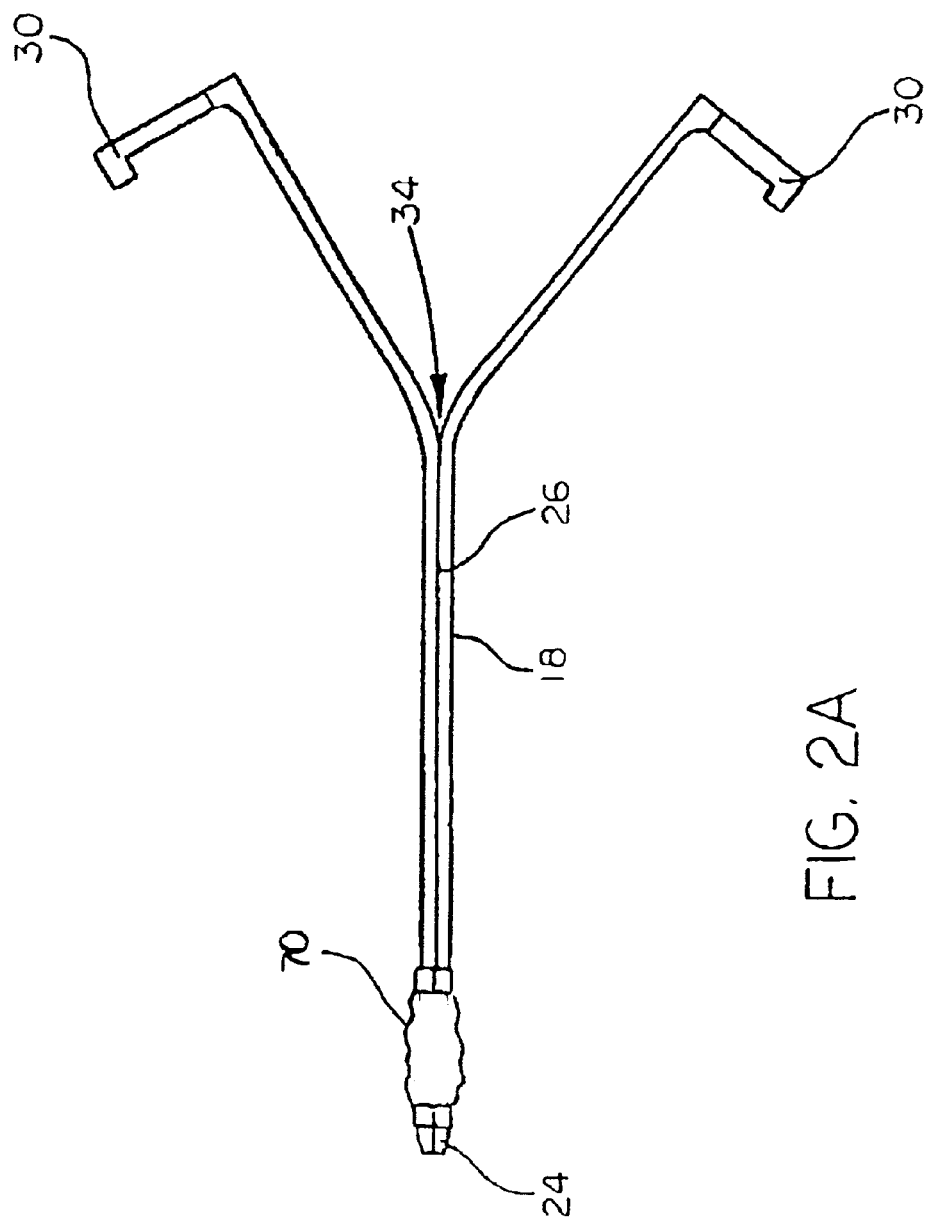
FIG. 2a is a side view of the splittable occlusion balloon sheath of FIG. 2 partially split.

The splittable occlusion balloon sheath (10) of the present invention as shown in FIGS. 1a, 1b and 2 assists in the introduction of specialized medical devices, such as pacemaker leads, defibrillator leads, or other diagnostic devices for medical treatment, into the coronary sinus of the human heart. The coronary sinus is the largest cardiac vein and serves as a conduit for access to various locations within the heart. Depending on the depth of insertion of a medical device into the coronary sinus, both the left and right atria and the left and right ventricles of the heart can be analyzed and treated from the coronary sinus. The coronary sinus is especially useful for the introduction of pacemaker leads designed to pace the left side of the heart.

Two approaches are commonly used for placement of a medical device within the coronary sinus, an inferior approach from below the heart, and a superior approach from above the heart. In the superior approach as shown in FIG. 1a, the device is advanced through either the internal jugular or subclavian vein through the superior vena cava into the right atrium until it is directed toward and into the coronary sinus. In the inferior approach, as shown in FIG. 1b, the device is advanced through the femoral vein through the inferior vena cava into the right atrium. The tip of the device is then directed toward in into the ostium of the coronary sinus. The superior approach is the preferred approach especially for the introduction of pacemaker leads into the coronary sinus. The inferior approach may be used for temporary placement of medical devices in the coronary sinus, such as for the temporary pacing of the heart.

Medical practitioners often monitor the introduction of medical devices and their progress through the vascular system by use of fluoroscopes. Unfortunately, fluoroscopes cannot easily identify specific features in the heart, in general, and the critically important structures of the right atrium, specifically, thus making placement of medical devices into the coronary sinus extremely difficult. In addition, placement of medical devices in the coronary sinus is especially difficult when the heart is beating, in particular, when the medical device to be introduced is a flexible, flaccid product, such as a pacemaker lead.

In addition to the difficulties associated with introducing medical devices into the coronary sinus, it is often difficult to retain those medical devices in the coronary sinus once the medical device has been introduced into the coronary sinus. Retention of medical devices in the coronary sinus is especially difficult because the coronary sinus walls are slippery, extensible, and tapered such that the vessels of the coronary sinus become smaller in the direction in which the medical device is advanced.

Further, conventional introducers or sheaths used for introducing these specialty medical devices, such as pacemaker leads, into the coronary sinus are limited in size to the size of the lumen of the introducer or sheath.

The structure and shape of the splittable occlusion balloon sheath (10) of the present invention addresses and solves these problems and permits the precise placement necessary for introduction of small, flexible medical devices, such as electrode leads, into the coronary sinus. In addition to the occlusion balloon (70) providing stability for the splittable occlusion balloon sheath when inflated within the coronary sinus, it also provides a means to inject a renograph dye in a retrograde direction within the coronary sinus. Features of this splittable occlusion balloon sheath (10) may include its splittable structure, the use of various types and shapes of occlusion balloon(s), the presence of a splittable hemostasis valve or partitioned hemostasis valve system, increased stiffness of the sheath (10) to minimize compression when positioned in tight bends, radiopaque tip markers, and vents. In addition, the preferred splittable occlusion balloon sheath (100) has a unique shape useful to assist in its introduction into the coronary sinus.

A first embodiment of the splittable occlusion balloon sheath (10) is formed from a generally elongated substantially cylindrical tube (18) having a handle (20) affixed to its proximal end (22) as shown in FIGS. 2, 2a, 3 and 3a. One preferred embodiment is disclosed in U.S. Pat. No. 5,098,392, incorporated herein by reference. The tube (18) is formed of a suitable plastic, preferably a high or low density polyethylene, tetrafluoroethylene, fluorinated ethylene-propylene plastic, wherein said plastic is compatible with body fluids. The tube has a proximal end (22) and a distal end (24). In addition, the tube has a pair of mechanically formed, longitudinally extending zones (26) of reduced thickness defined by internally scored longitudinal shallow grooves or indentations, running throughout the length of the tube. See FIGS. 2, 2a, and 3a. These mechanically formed, reduced thickness zones permit the introducer sheath to be "split" following use. Although other known methods of splitting the introducer sheath are within the scope of the invention, the above referred to method is preferred.

The handle (20) includes a pair of handle members (30) which project laterally outward from the cylindrically shaped tube engaging said tube (18), as shown in FIG. 2. Each handle member (30) is secured to the proximal end (22) of the introducer sheath by conventional securing methods. Each handle member (30) defines one-half of the handle (20). Each of the handle members (30) are secured to the tube (18) at a location which permits easy splitting of the tube by pressure on the top surface (32) of each of the handle members as they are pulled away from the surface of the tube. To assist in the easy splitting of the tube, the top surface (32) of each of the handle members is also ribbed. The handle members are extended, preferably, at least about 0.5 in. (1.3 cm) from the surface of the tube for ease of use. The tube (18) extends proximally to the surface of the handle (30) to form a lumen (34) running the length of the tube (18) through which a dilator (50), such as is disclosed in FIG. 5, can be inserted.

Figure 4C:
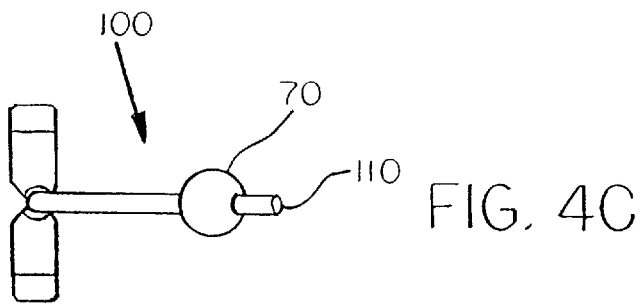
FIG. 4c is an end view of the splittable occlusion balloon sheath of FIG. 4a viewed from its distal end.
Figure 4A:
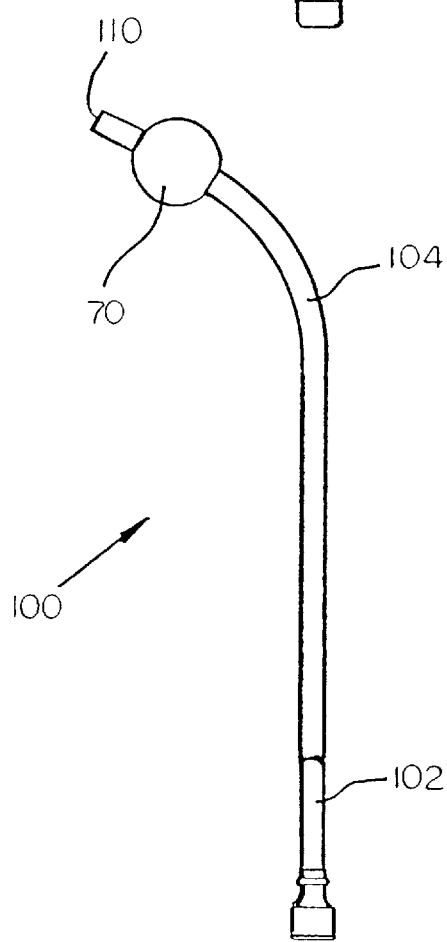
FIG. 4a is a side view of a second embodiment of a splittable occlusion balloon sheath containing a precurved distal section specially designed for a superior approach to the coronary sinus with the occlusion balloon inflated.
Figure 4B:
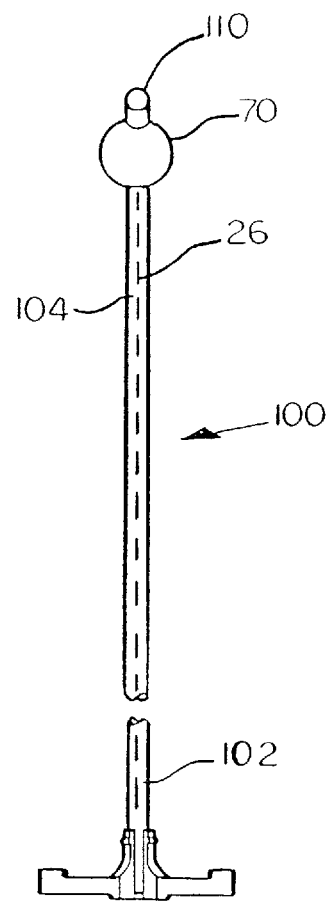

In a preferred embodiment as shown in FIGS. 4a, 4b and 4c, the splittable occlusion balloon sheath (100) for use in a superior approach to the coronary sinus has a precurved shape which assists in its introduction into the coronary sinus. This precurved, splittable occlusion balloon sheath (100) is produced utilizing a conventional sheath manufacturing process, and is preferably formed from a single, unitary structure.

As shown in FIGS. 4a, 4b and 4c, the precurved, splittable occlusion balloon sheath (100) for use in a superior approach to the right atrium preferably includes a generally straight proximal section (102) and a precurved distal section (104). The overall length of the splittable occlusion balloon sheath (100) can range from about 12 inches (30 cm) to about 50 inches (120 cm), depending upon the size and age of the patient, although the sheath (100) obviously cannot be longer than the medical device, such as electrode leads, which are introduced through the lumen in the splittable occlusion balloon sheath (100). The proximal section (102) of this splittable occlusion balloon sheath (100) is preferably a conventional, hollow, generally straight sheath introducer section of sufficient length for introduction into the patient. Preferably its length is from about 0.2 in. (0.5 cm.) to about 15 in. (38 cm.), preferably from about 0.5 in. (1 cm.) to about 5 in. (12 cm.) in length. However, the splittable occlusion balloon sheath (100) may contain no generally straight proximal section (102), but rather be curved over its entire length.

Merged with the distal end of the proximal section (102) of the precurved, splittable occlusion balloon sheath (100), is the precurved distal section (104), as shown in FIG. 4a. In one embodiment, the precurved distal section (104) may be comprised of two or more separate curved sections and/or straight sections. However, in a preferred embodiment the precurved distal section (104) is comprised of a single, continuous curve, curving through an arc of about 20 to about 120 degrees, preferably from about 30 about 100 degrees, and more preferably from about 40 to about 80 degrees with a radius from about 0.5 in. (1.2 cm) to about 2.0 in.(5.1 cm), preferably from about 0.8 in. (2.0 cm) to about 1.5 in. (3.8 cm). At the distal end of the precurved distal section (104) is a tip (110) for the precurved, splittable occlusion balloon sheath (100). This tip (110) can be softened to reduce the likelihood of damage to the tissue during use. In a preferred embodiment, the precurved distal section (104) curves in the same general direction along its entire length, i.e., it is substantially coplanar (within about 15 degrees of coplanar), though minor variations outside of a plane formed by this precurved distal section (104) are within the scope of the invention.

As a further alternative embodiment of the splittable occlusion balloon sheath (100), any combination of curves or curved and straight sections is acceptable which results in an overall shape for the distal section of the splittable occlusion balloon sheath (100) which is similar to the shape of the preferred embodiment earlier described and which causes the distal tip (110) of the splittable occlusion balloon sheath (100) to enter the coronary sinus after introduction into the right atrium.

Figure 7C:
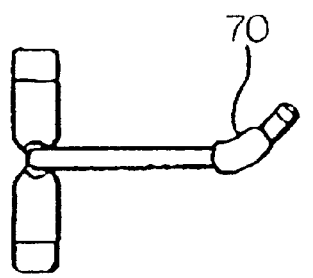
FIG. 7c is an end view of the splittable occlusion balloon sheath of FIG. 7a viewed from its distal end.
Figure 7A:
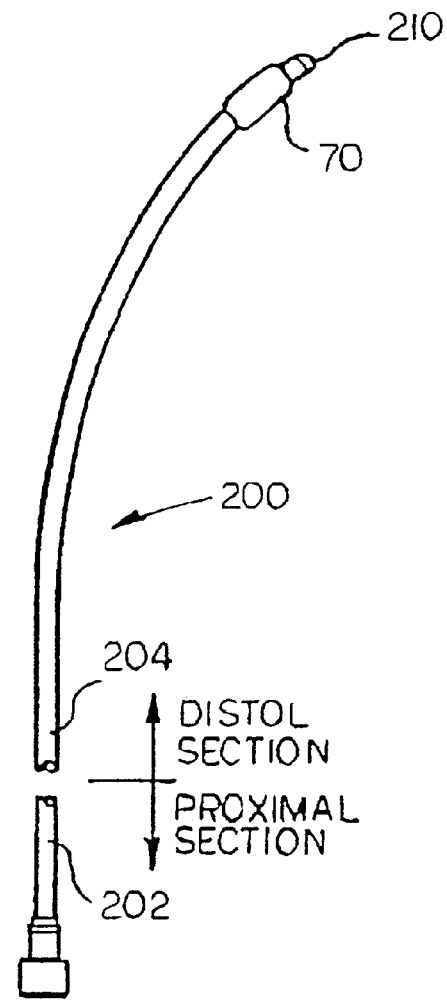
FIG. 7a is a side view of a third embodiment of a splittable occlusion balloon sheath containing a precurved distal section specifically designed for an inferior approach to the coronary sinus.
Figure 7B:
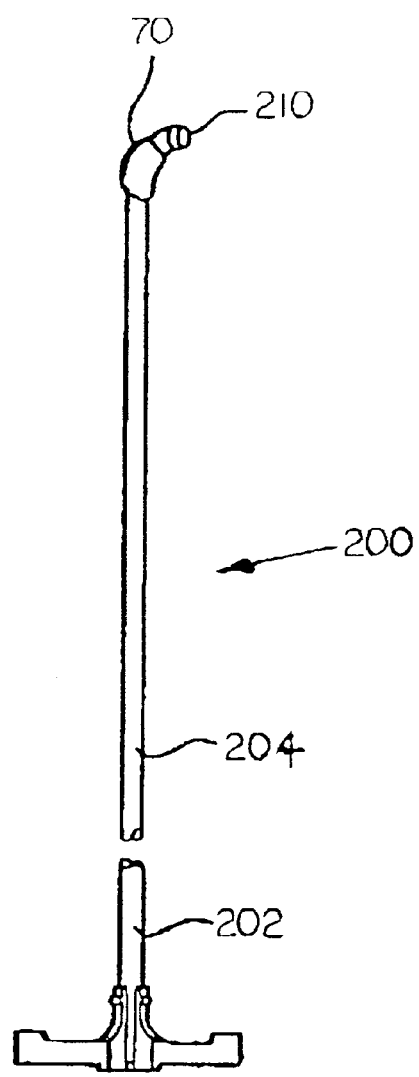

In a further preferred embodiment of the splittable occlusion balloon sheath (200) shown in FIGS. 7a, 7b and 7c, when an inferior approach to the coronary sinus is utilized for introducing the precurved, splittable occlusion balloon sheath (200) into the heart, a different preferred shape of the splittable occlusion balloon sheath (200) is utilized. In addition, the splittable occlusion balloon sheath (200), as a whole and specifically the first proximal section (202) of the device, are preferably longer than the length of the precurved, splittable occlusion balloon sheath (100) of the first preferred embodiment shown in FIGS. 4a, 4b and 4c. In this further preferred embodiment as shown in FIGS. 7a, 7b and 7c, the distal section (204) shown in FIG. 7a is comprised of a single, continuous curve, curving through an arc of about 30 to about 100 degrees, preferably from about 40 to about 80 degrees, and more preferably from 40 to about 80 degrees, with a radius of about 0.5 in. (1.2 cm.) to about 2.0 in. (5.1 cm.), preferably from about 0.8 in. (2.0 cm.) to about 1.5 in. (3.8 cm.). At the distal end of the precurved distal section (204) is the tip (210) of the splittable occlusion balloon sheath (200). In addition, this distal section (204) also curves out of its plane in an amount from about 15 to about 90 degrees, and preferably from about 30 to about 75 degrees as shown in FIGS. 7b and 7c. This out-of-plane curve permits easier placement of the distal tip (210) of this splittable occlusion balloon sheath (200) into the coronary sinus when an inferior approach is utilized than is permitted by the design of the first preferred embodiment of FIGS. 4a, 4b and 4c. The distal curved section (204) of this embodiment may be formed in any manner which results in the same general shape for the splittable occlusion balloon sheath (200) and which directs the distal tip (210) of the splittable occlusion balloon sheath (200) into the coronary sinus after introduction into the right atrium. These combinations may also include any combination of curved or straight sections which when combined result in the same general, overall shape as that of the distal section (204) of the splittable occlusion balloon sheath (200) of this alternative embodiment.

The distal canted tip (24, 110, 210) of the splittable occlusion balloon sheath (10, 100, 200) may be, and preferably will be, tapered to form a good transition with a dilator. This tapering is preferably less than 10 degrees, and more preferably, about 4 degrees to about 7 degrees. The splittable occlusion balloon sheath (10, 100, 200) preferably may also contain one or a multitude of radiopaque tip marker bands near the distal tip (24, 110, 210) of the splittable occlusion balloon sheath (10, 100, 200) or it may be radiopaque throughout its entire length. This can be accomplished by utilizing conventional material additives, such as barium sulfate.

This splittable occlusion balloon sheath (10, 100, 200) may also contain one or a plurality of vents near its distal tip. However, in a preferred embodiment, no vents are utilized in the device. If vents are used at all, they should be located no more than about one inch from the distal tip of the splittable occlusion balloon sheath and preferably from about 0.1 in. (0.2 cm.) to about 1.0 in. (2.5 cm.) from the tip.

While the splittable occlusion balloon sheath (10, 100, 200) may be made of any biocompatible material suitable for use in humans which has a memory or permits distortion from and substantial return to the desired three dimensional shape, such as polyethylene or polyurethane, in a preferred embodiment it is made of a material compatible to that used to produce the occlusion balloon (70), which is discussed in more detail later.

In a preferred embodiment, the distal tip (24, 110, 210) of the splittable occlusion balloon sheath (10, 100, 200) may be made of a more pliable, more compressible material, than the remaining length of the splittable occlusion balloon sheath (10, 100, 200) to prevent damage to the vasculature and the coronary sinus when in use.

For the purpose of illustration and not limitation, the internal diameter of the splittable occlusion balloon sheath (10, 100, 200) may vary from about 4 to about 16 French (1 French equals ⅓ of a millimeter). Such splittable occlusion balloon sheaths (10, 100, 200) can thus accept dilators whose outside diameter is from about 4 to about 16 French. Obviously, if larger or smaller dilators or other medical devices are used in combination with the splittable occlusion balloon sheath (10, 100, 200), modifications in size and shape of the splittable occlusion balloon sheath (10, 100, 200) can be made.

The splittable occlusion balloon sheath (10, 100, 200) of the invention is preferably multi-lumened. The splittable occlusion balloon sheath (10, 100, 200) preferably contains at least two (2) lumen (72, 74), as shown on FIG. 11, one for introduction of contrast media (74) and various medical devices out the distal tip (24, 110, 210) of the splittable occlusion balloon sheath, and one (72) for introduction of a media for inflation of the occlusion balloon (70). Alternatively, if more than one balloon is used to occlude the coronary sinus, additional lumen may be used for this inflation procedure. Additional lumen may also be used for other conventional processing through the splittable occlusion balloon sheath (10, 100, 200).

Variations in size and shape of the splittable occlusion balloon sheath (10, 100, 200) are also intended to encompass pediatric uses of the present invention, although the preferred uses are in adult human hearts. It is well recognized that pediatric uses may require reductions in size of the various sections of the splittable occlusion balloon sheath (10, 100, 200), in particular shortening the first, proximal section (102, 202), but without any significant modification to the shape or curvature of the second, distal section (104, 204) of the splittable occlusion balloon sheath (100, 200). In addition, variations in size or shape are also intended to encompass specialized situations that sometimes occur in patients with enlarged or rotated hearts.

The structure of the splittable occlusion balloon sheath (10, 100, 200) should be stiff enough to prevent substantial movement of the distal section (104, 204) of the splittable occlusion balloon sheath (100, 200) once in place within the heart and to retain its general shape. In order to permit good torque control, the first, proximal section (102, 202) may be made stiffer than the distal section (104, 204). This stiffer construction can be achieved by conventional construction techniques, such as increasing the thickness of the material or manufacturing a portion of the splittable occlusion balloon sheath (100, 200) from a material possessing characteristics of enhanced stiffness, such as by adding a metal component, a stiffener material or by fusing different materials together. The second, distal section (104, 204) of the splittable occlusion balloon sheath (100, 200) should be stiff, but flexible. This permits this curved, distal section (104, 204) to be straightened when a straight dilator (50) is passed through its lumen to facilitate introduction into the patient's vasculature and passage through the vasculature into the right atrium.

Figure 5:
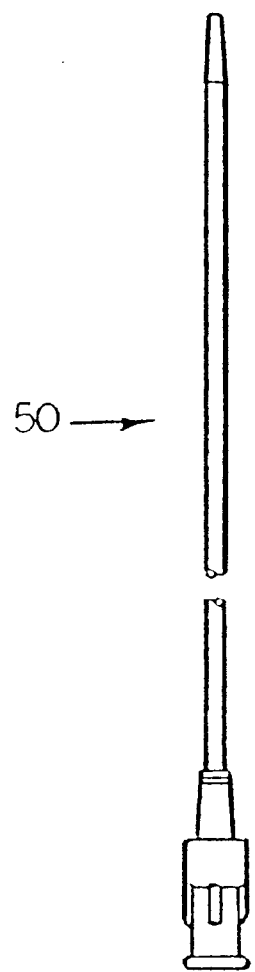
FIG. 5 is a side view of a straight dilator for use with the splittable occlusion balloon sheath.
Figures 6A, 6B, 6C:
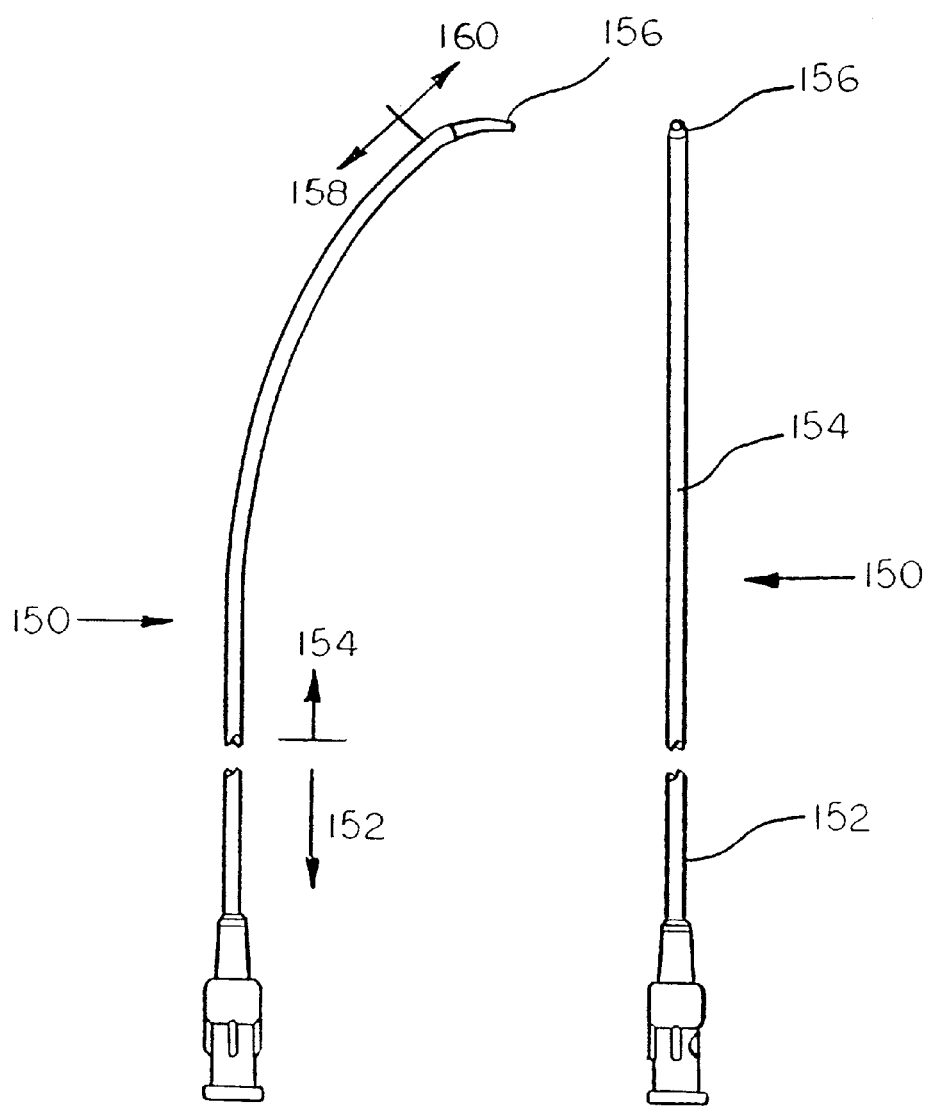
Figures 8A, 8B, 8C:
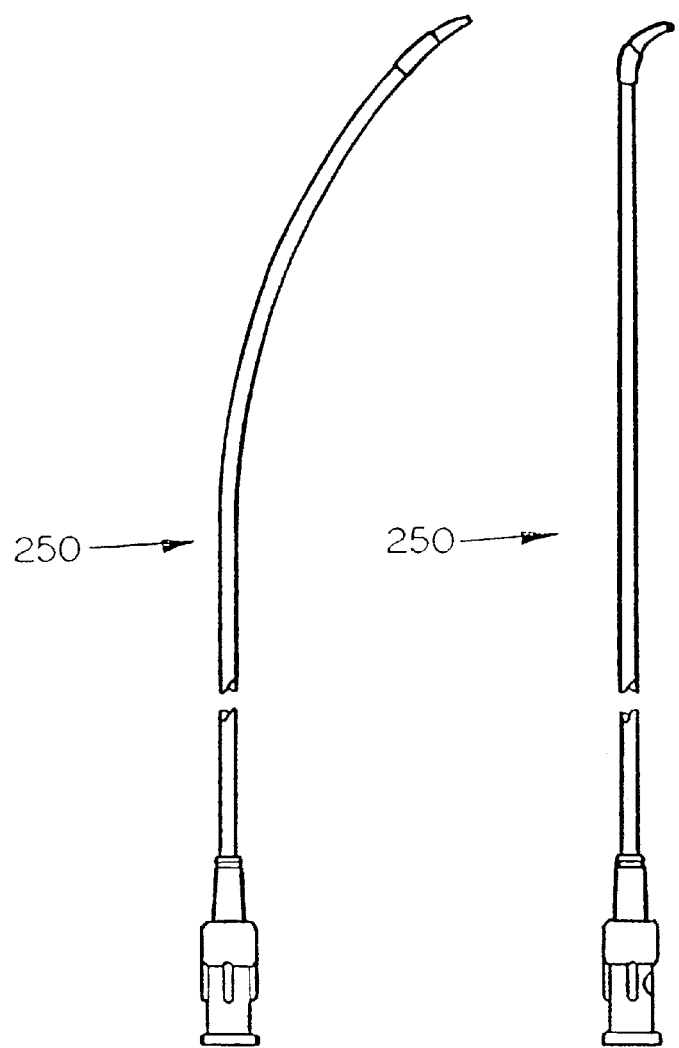

The stiffness of the splittable occlusion balloon sheath (10, 100, 200) can also be enhanced by insertion of a conventional straight dilator (50) as shown in FIG. 5 or a precurved dilator (150, 250), as shown in FIGS. 6a and 8a, or shaped catheter within a lumen of the splittable occlusion balloon sheath (10, 100, 200). (A "dilator" is an inner strengthening element intended to be removed to allow placement of the sheath.) The dilator (50, 150, 250) acts as a stiffening means for stiffening the structure of the splittable occlusion balloon sheath. The dilator (50, 150, 250) is produced from conventional dilator material and preferably contains a lumen passing therethrough for use with a guidewire. In a preferred embodiment as shown in FIGS. 6a, 6b and 6c for a superior approach to the coronary sinus, the shape of the precurved dilator (150) is precurved. The precurved dilator (150) when precurved and used with the preferred, precurved splittable occlusion balloon sheath (100), allows for entry of the precurved dilator (150) into the coronary sinus using the superior approach. In fact, in a preferred embodiment, after the precurved dilator (150) and the splittable occlusion balloon sheath (100) have entered the right atrium, a distal section (154) of the precurved dilator (150) is extended from the distal tip (110) of the splittable occlusion balloon sheath (100) to enter the coronary sinus prior to entry into the coronary sinus of the splittable occlusion balloon sheath (100). In order to effect this entry into the coronary sinus, in a preferred embodiment, the shape of the precurved dilator (150) is precurved, as shown in FIG. 6a. The overall length of the dilator (150) can range from about 12 in. (30 cm.) to about 50 in. (125 cm.), depending on the size and the age of the patient and the length of the precurved splittable occlusion balloon sheath (100) that is used. Preferably this precurved dilator (150) has a proximal section (152), a distal section (154), and a softened tip (156). The proximal section (152) of this precurved dilator (150) is preferably a conventional, generally straight dilator section of sufficient length for introduction into the patient. Merged with the distal end of the proximal section (152) of the dilator (150) is the precurved, distal section (154), as shown in FIG. 6a. In a preferred embodiment the precurved distal section (154) is comprised of two separate curved sections (158 and 160). In a preferred embodiment the first curved section (158) curves through an arc of about 10 to about 60 degrees, preferably from about 15 to about 50 degrees, and most preferably from about 25 to about 45 degrees, with a radius of about 2 in. (5.1 cm.) to about 5 in. (12.7 cm.), preferably from about 3.0 in. (7.6 cm.) to about 4.0 in. (10.2 cm.). At the distal of end of this first curved section (158) is the second curved section (160) which ends at the distal tip (156) of the precurved dilator (150). This second curved section (160) curves through an arc of about 20 to about 90 degrees, preferably from about 30 to about 80 degrees, and most preferably from about 50 to about 70 degrees, with a radius of the arc from about 0.2 in. (0.5 cm.) to about 2 in. (5.1 cm.) and more preferably from about 0.2 in. (0.5 cm.) to about 1 in. (2.6 cm.). Alternatively, the curves of the first curved section (158) and the second curved section (160) can be modified such that the sum of the arcs of these curves is from about 30 to about 120 degrees, preferably from about 45 to about 110 degrees, with appropriate radii, which allow the distal tip (156) of the precurved dilator (150) to enter the coronary sinus in the same manner as the precurved dilator (150) with the pair of curved sections (158, 160). In a preferred embodiment, the second curved section (160) is an extension of the first curved section (158) and curves in the same general direction as the first curved section (158), resulting in the first and second curved sections (158, 160) being substantially planar (within about 15 degrees of coplanar), though minor variations outside the plane formed by the curves are certainly within the contemplation of the invention.

In an alternative preferred embodiment of this precurved dilator (150), the first and second curved sections (158, 160) can be combined into a single curve whose arc is between about 20 and about 120 degrees, preferably from about 40 to about 115 degrees, and most preferably from about 45 to about 90 degrees, with a radius of about 2.0 in. (5.1 cm.) to about 6.0 in. (15.3 cm.), preferably about 3 in. (7.6 cm.) to about 5.0 in. (12.7 cm.) In this alternative embodiment the first and second curves (158, 160) from the earlier embodiment as shown in FIG. 6a are combined into a single curve.

As a further alternative embodiment of the precurved dilator, any combination of curves or curved and straight sections is acceptable which results in an overall shape for the distal section (154) of the precurved dilator (150) which is similar to the shapes of the preferred embodiments above described and which causes the distal tip (156) of the precurved dilator (150) to enter the coronary sinus after introduction into the right atrium.

The distal tip (156) of the precurved dilator (150) is preferably a rounded, instead of the more pointed tip present in conventional dilators. Further, it should be more softened than conventional dilator tips. By rounding this tip (156) and softening it, it is less likely to cause damage to tissue located within the patient's body, particularly in the coronary sinus.

In an alternative embodiment for an inferior approach to the coronary sinus the shape of the precurved dilator (250) as shown in FIGS. 8a, 8b and 8c conforms to that of the splittable occlusion balloon sheath (200) as shown in FIGS. 7a, 7b and 7c.

If desired, the shape of the dilator (50) used for introduction of the splittable occlusion balloon sheath into the patient and for manipulation to a point near the right atrium can be straight as shown in FIG. 5, such that upon introduction into the lumen of any of the shaped, splittable occlusion balloon sheaths discussed above (100, 200), the overall shape of the splittable occlusion balloon sheath (100, 200) is straightened. When the dilator (50) is then removed from the lumen of the shaped, splittable occlusion balloon sheath (100, 200), the splittable occlusion balloon sheath (100, 200) returns to its predetermined shape.

Using any of these embodiments for a combination of the dilators (50, 150, 250) with the splittable occlusion balloon sheaths (10, 100, 200) result in a combination device formed in different shapes that may be useful for introduction into the patient, for manipulation from the point of entry through vasculature into the right atrium and into the coronary sinus itself.

In a preferred embodiment, the splittable occlusion balloon sheath (10) also includes a hemostasis valve incorporated into a lumen of the splittable occlusion balloon sheath (10). In a preferred embodiment, the hemostasis valve incorporated into the splittable occlusion balloon sheath is a splittable hemostasis valve, such as is disclosed, for example, in U.S. Pat. Nos. 5,312,355, 5,125,904, 5,397,311, 5,441,504, 5,755,693, and 5,613,953.

Figure 9:
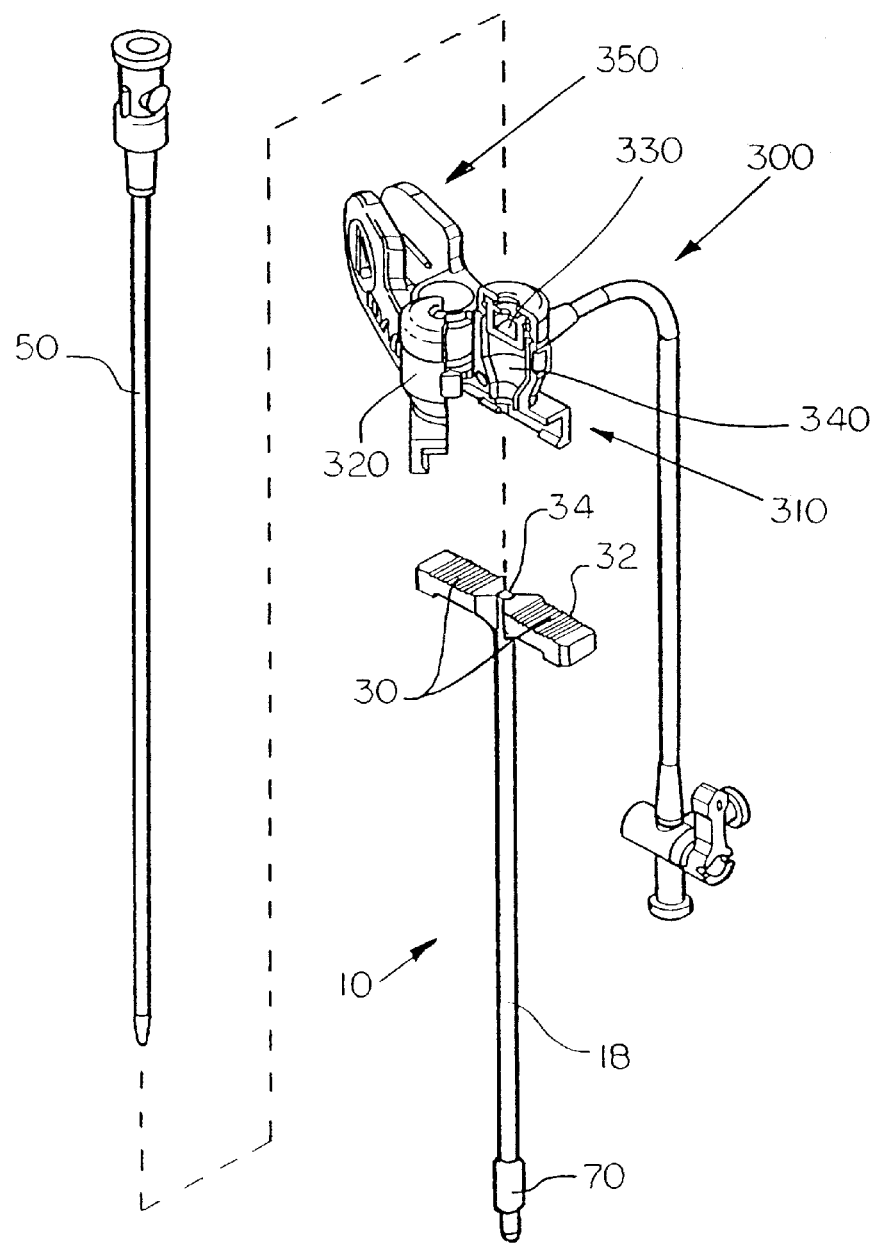
FIG. 9 is a side perspective exploded view of the splittable occlusion balloon sheath for use with a partitioned hemostasis valve system and a straight dilator.

In a more preferred embodiment, however, a SEALA-WAY™ partitioned hemostasis valve system (300), designed by Daig Corporation, and disclosed in Ser. No. 09/207,295, filed Dec. 8, 1998 and assigned to the common assignee, which disclosure is incorporated herein by reference, is preferred for utilization with the splittable occlusion balloon sheath (10, 100, 200) as shown in FIG. 9. The partitioned hemostasis valve system (300) includes a partitioned hemostasis valve housing (320), a partitioned hemostasis valve (330) secured within a central chamber (340) within that housing (320), a hemostasis valve separation system (350) forming an element of the partitioned hemostasis valve housing (320), and an adaptor system (310), secured to the partitioned hemostasis valve housing (320), by which the splittable sheath (10, 100, 200) can be secured to the partitioned hemostasis valve system (300). This partitioned hemostasis valve system (300) provides hemostasis while still allowing access to the lumen of the splittable occlusion balloon sheath (10, 100, 200) and therefore also to the vasculature. In addition, it provides more flexibility than using conventional splittable hemostasis valves because it can be secured to the splittable occlusion balloon sheath (10, 100, 200) prior to the beginning of the medical procedure, before the splittable occlusion balloon sheath (10, 100, 200) has been inserted into the vasculature of the patient, or it can be secured to the splittable occlusion balloon sheath (10, 100, 200) after the splittable occlusion balloon sheath (10, 100, 200) has been advanced through the vasculature to the heart. Further, the partitioned hemostasis valve system (300) can also be removed from the splittable occlusion balloon sheath (10, 100, 200) before the procedure has been completed, or after the procedure has been completed, at the discretion of the physician.

An important feature of the present invention is the occlusion balloon (70) that is secured at or near the distal end (24) of the splittable occlusion balloon sheath (10), as shown in FIG. 4a. While conventional occlusion balloons may be utilized for this invention, in a preferred embodiment, the occlusion balloon (70) is specially designed to be securable to the splittable sheath.

The occlusion balloon (70) may be molded of an elastomeric material, such as a polyurethane, silicone, or latex. However, in a preferred embodiment, the occlusion balloon (70) is preferably made of a nonextensible balloon material, such as high or low density polyethylene, polyethylene teryphthalate, polyester, polyester copolymers, polyamide or polyamide copolymers. In a more preferred embodiment, the balloon is manufactured of a material that is "compatible" with the material from which the cylindrical tube (18) of the splittable occlusion balloon sheath (10) is manufactured so that it can be secured to the surface of the cylindrical tube (18) of the splittable occlusion balloon sheath (10) without using an additional adhesive. "Compatible" means that the material from which the occlusion balloon (70) is formed mixes on a molecular level scale with the material from which the tube (18) from which the splittable occlusion balloon sheath (10) is formed, and crystallizes homogeneously. Thus, while the material from which such components are constructed may not have precisely the same softening point, they should have softening points which are consistent so that the materials will mix on a molecular level. Preferably the softening point for the occlusion balloon (70) should be at a slightly lower temperature than that for the tube (18) of the splittable occlusion balloon sheath (10), so that as the occlusion balloon (70) is formed, it can then be bonded directly to the tube (18) of the splittable sheath (10). In one preferred embodiment, the occlusion balloon (70) is formed from a linear low density polyethylene material, while the tube (18) of the splittable occlusion balloon sheath is formed from a high density polyethylene material. Alternatively, the occlusion balloon (70) may be joined to the cylindrical tube (18) of the splittable occlusion balloon sheath (10) by use of an adhesive or other conventional process for the joining of two plastic materials.

Figure 3:
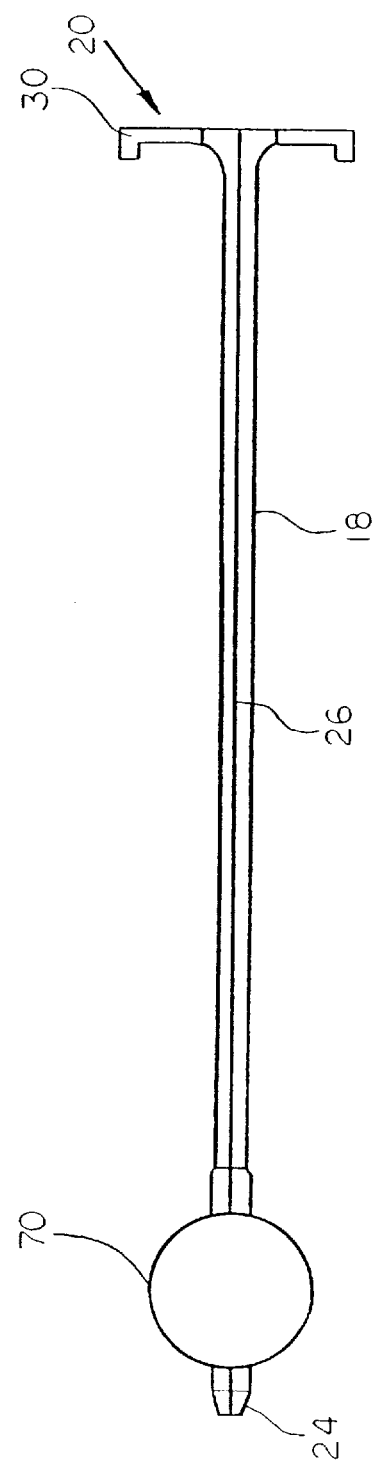
FIG. 3 is a side view of the splittable occlusion balloon of FIG. 2 sheath with the occlusion balloon inflated.

The occlusion balloon (70) has a collapsed profile against the splittable sheath (10) for insertion into the vessels of the human body as shown in FIG. 2, and an expanded profile as shown in FIG. 3 for occluding the coronary sinus with the expanded profile diameter being from about 2 to about 10 times, and preferably 3 to 10 times the collapsed profile diameter. Preferably the occlusion balloon (70) in collapsed profile is from about 0.2 in. (0.5 cm.) to about 2.0 in. (5.0 cm.) in length, and about 0.05 in.(0.1 cm.) to about 0.5 in. (1.1 cm.) in width. When fully expanded the occlusion balloon (70) preferably is at least about 0.2 in. (0.5 cm.) in length and preferably from about 0.2 in. (0.5 cm.) to about 2.0 in. (5.0 cm.) in length, and about 0.25 in. (0.6 cm.) to about 1.0 in. (2.5 cm.) in width. The wall thickness of the occlusion balloon (70) ranges from about 0.0005 in. (0.001 cm.) to about 0.005 in. (0.01 cm.) when not inflated.

Figure 11:
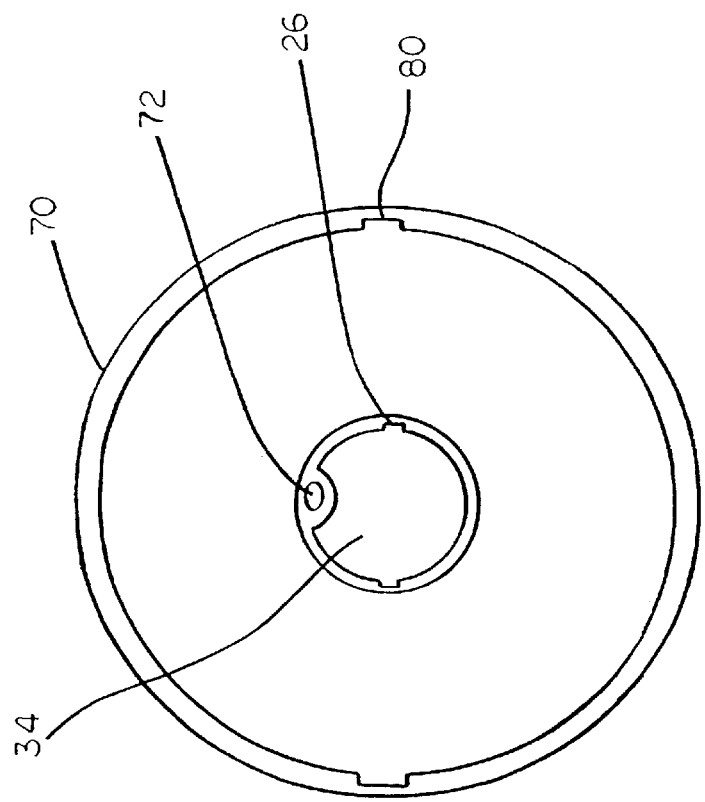
FIG. 11 is a front end view of the splittable occlusion balloon sheath of FIG. 10a showing the score line on the internal surface of the occlusion balloon.

Preferably, the splittable occlusion balloon sheath (10) has an inflation lumen (72) as shown in FIG. 11 extending from proximal end (22) near or to the distal end (24) of the splittable occlusion balloon sheath (10). In a preferred embodiment this inflation lumen (72) is configured to allow inflation of the balloon with a liquid, such as a mixture of the saline solution and radiographic contrast medium. Alternatively and preferably, a gas may also be used for the inflation of the occlusion balloon (70). Although the use of a separate lumen (72) for the inflation of the occlusion balloon (70) is preferred, the occlusion balloon (70) may also be inflated at the same time that the contrast medium is introduced through the lumen of the splittable occlusion balloon sheath (10). In this embodiment the balloon (70) is inflated by the flow of the contrast medium through a lumen (34) of the splittable occlusion balloon sheath (10). Thus, the lumen (34) of the splittable occlusion balloon sheath (10) for introduction of the contrast medium is in fluid communication with the occlusion balloon (70). As pressurized fluid is forced through the lumen (34) of the splittable occlusion balloon sheath (10), it enters and inflates the inflatable occlusion balloon (70).

The shape of the occlusion balloon (70) when inflated can be any conventional shape which occludes the coronary sinus. However, in a preferred embodiment, the shape of the balloon (70) when inflated circumferentially surrounds the tube (18) of the splittable occlusion balloon sheath (10) in a spherical shape as shown in FIGS. 3, 10a and 10b. By having an occlusion balloon (70) that inflates concentrically around the splittable sheath (10), the distal tip (24) of the splittable occlusion balloon sheath (10), which extends beyond the balloon (70), is placed near the center of the channel in the coronary sinus.

This concentric shape for the occlusion balloon (70) can be achieved by any conventional occlusion balloon system. In one preferred embodiment, as shown in FIGS. 10a and 10b, a single balloon (70) is utilized which is circumferentially secured to the body of the splittable occlusion balloon sheath (10) around its outside surface. Preferably the locations for securing the occlusion balloon (70) to the body of the splittable occlusion balloon sheath (10) are consistent with the zones of reduced thickness (26) in the surface of the splittable occlusion balloon sheath (10), so that upon splitting of the splittable occlusion balloon sheath (10) the occlusion balloon (70) also splits at these locations. Also preferably, as shown in FIGS. 10c and 10d, the surface of the balloon (70) may be secured to the surface of the cylindrical tube (18) of the splittable occlusion balloon sheath (10) proximal and distal from the inflated portion of the balloon. This forms bond areas (74, 76) on the cylindrical tube (18) of the splittable occlusion balloon sheath (10) where the balloon (70) is secured in place. Any other method of securing the occlusion balloon (70) to the surface of the cylindrical tube (18) of the splittable occlusion balloon sheath (10) which allows for the occlusion balloon (70) to be split upon the splitting of the splittable occlusion balloon sheath (10) is within the scope of the invention.

Various mechanisms can be utilized for splitting of the occlusion balloon (70) into two separate and distinctive sections. For example, a physical zone of weakness or score line (80), as shown in FIG. 11, may be built into the wall of the occlusion balloon (70) such that upon pressure being applied to the walls of the occlusion balloon (70), it splits along these zones of weakness or score lines (80). These zones of weakness or score lines (80) in the surface of the balloon can be caused by physical mechanisms or by a chemical reaction or by radiation against the material used for construction of the occlusion balloon (70). Any method which permits the division of the balloons into separate sections as the splittable occlusion balloon sheath (10) is being split is within the disclosure of the invention.

In an alternative embodiment, a pair of balloons (170, 172) can be utilized, one secured on each side of the splittable occlusion balloon sheath (10) as shown in FIGS. 12a, 12b, 12c, and 12d. When these two balloons (170, 172) are utilized, they are preferably secured to the splittable occlusion balloon sheath (10) at locations distant from the zones of reduced thickness (26) in the splittable occlusion balloon sheath (10) so that upon splitting of the splittable occlusion balloon sheath (10), one balloon (170) is retained with one-half of the splittable occlusion balloon sheath (10) and the other balloon (172) is retained with the other half of the splittable occlusion balloon sheath (10).

Figure 13D:
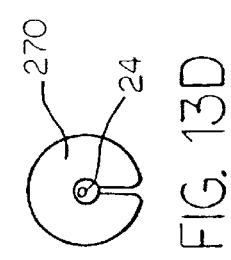

In a further alternative embodiment as shown in FIGS. 13a, 13b, 13c, and 13d, a single side-mounted eccentric occlusion balloon (270) is utilized. In this embodiment the occlusion balloon (270) is secured at a single location to the surface of the splittable sheath (10). Upon inflation of this single occlusion balloon (270), it preferably encircles the splittable sheath, as shown in FIG. 13d, to form a generally concentric shape which places the distal tip (24) of the splittable sheath (10) at a location near the center of the channel in the coronary sinus. Preferably this single occlusion balloon (270) circumscribes the splittable occlusion balloon sheath (10) at least about 270 degrees.

Other shapes for eccentric balloons may also be utilized which do not place the distal tip of the splittable occlusion balloon sheath (10) in the center of the coronary sinus, if that is preferred by the physician. For example, a single, side-mounted, eccentric balloon (370) can be used where the distal tip (24) of the splittable occlusion balloon sheath (10) is not centered within the coronary sinus by the inflation of the balloon (370) which is shown in FIGS. 14a, 14b, 14c, and 14d. In this embodiment, the occlusion balloon (370) preferably circumscribes the splittable occlusion balloon sheath (10) less than 270 degrees.

Figure 15B:
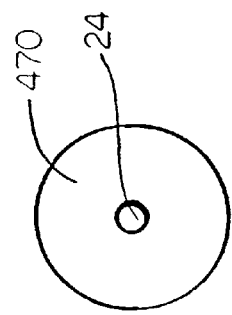
Figure 15A:
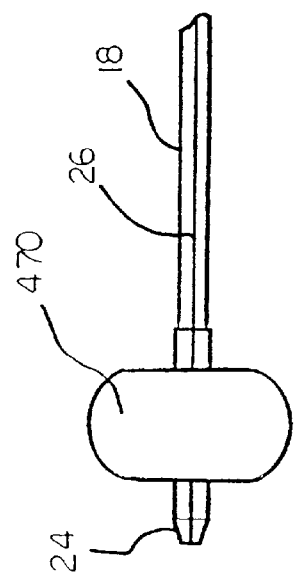
FIG. 15a is a side cutaway view of the distal portion of the splittable occlusion balloon sheath showing the use of a single, circumferential, concentric "doughnut-shaped" occlusion balloon.
Figure 17B:
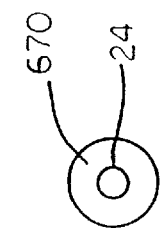
Figure 17A:
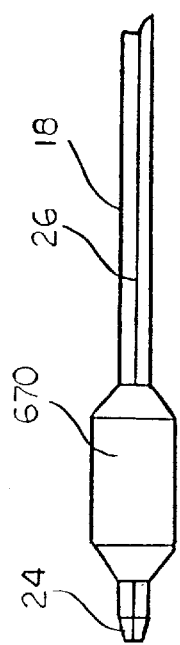
FIG. 17a is a side cutaway view of the distal portion of the splittable occlusion balloon sheath showing the use of a single, circumferential, concentric, cylindrical occlusion balloon.

Other shapes for a concentric occlusion balloon may also be used. For example, in a preferred embodiment a single, spherical, circumferential, concentric occlusion balloon (70) is disclosed in FIGS. 10a and 10b. Alternatively, a single circumferential, concentric, "doughnut-shaped", occlusion balloon (470) can be utilized, as shown in FIGS. 15a and 15b. In another alternative embodiment, as shown in FIGS. 16a and 16b, a single, circumferential, concentric, conical occlusion balloon (570) can be utilized. In a further alternative embodiment, as shown in FIGS. 17a and 17b, a single, circumferential, concentric, cylindrical occlusion balloon (670) can be utilized.

Any other shape for the balloon or balloons that assists in the placement of the splittable occlusion balloon sheath (10) at the correct location within the coronary sinus, and assists in providing stability for that splittable occlusion balloon sheath (10) is within the scope of the invention.

In order to retain the occlusion balloon (70) within the coronary sinus, the outside surface of the occlusion balloon (70) may be treated to enhance its frictional contact with the coronary sinus. For example, structures disclosed in various patents, such as U.S. Pat. Nos. 5,807,326, 5,720,726, and 4,927,412 may be utilized to enhance the friction of the occlusion balloon (70) within the inner surface of the coronary sinus. Other well known methods to enhance frictional contact are also within the scope of the invention.

In operation, a modified Seldinger technique is used for insertion of the splittable occlusion balloon sheath (10) into the human body. once the opening is provided in the vasculature, a guidewire is inserted and advanced through the vasculature into the chamber of the heart where the medical procedure is to be performed. In a preferred embodiment of this invention using the superior approach to the right atrium as shown in FIG. 1a, the guidewire is advanced through the internal jugular or subclavian vein through the superior vena cava into the right atrium. The splittable occlusion balloon catheter (10, 100), preferably with a straight dilator (50) present in its lumen, is passed over the guidewire into the right atrium.

When the inferior approach is utilized as shown in FIG. 1b, the guidewire is advanced up through the femoral vein through the inferior vena cava into the right atrium. The splittable occlusion balloon sheath (200) with straight dilator (50) is advanced over the guidewire into the right atrium. The guidewire is then removed. The splittable occlusion balloon sheath (200) is then advanced under fluoroscopic guidance toward the tricuspid valve with the tip of the splittable occlusion balloon sheath (200) pointing medially as shown in FIG. 1*b*.

When the splittable occlusion balloon sheath (100) as shown in FIG. 4*a* is curved in a preferred curvature, the preferred dilator (150), as shown in FIG. 6*a*, used in conjunction with the preferred splittable occlusion balloon sheath (100) permits ease in locating the ostium of the coronary sinus using the superior approach. In this procedure, a straight dilator (50) is first introduced within a lumen within the splittable occlusion balloon sheath (150) to straighten out the curve present in that splittable occlusion balloon sheath (150). In a preferred embodiment the combination precurved splittable occlusion balloon sheath (100) over straight dilator (50) is advanced over the guidewire through the vasculature into the right atrium of the heart. At this point, in a preferred embodiment the straight dilator (50) is replaced by the precurved dilator (150), resulting in a fixed curve in the system. The distal tip (156) of the precurved dilator is then advanced away from the distal tip (110) of the precurved splittable occlusion balloon sheath (100) until it enters the coronary sinus. The splittable occlusion balloon sheath (100) is then advanced over the precurved dilator (150) until its distal tip (110) also enters the coronary sinus. The precurved dilator (150) can then be removed from the precurved splittable occlusion balloon sheath (100).

Once the distal end of the splittable occlusion balloon sheath (10, 100, 200) has been placed within the coronary sinus, the occlusion balloon(s) (70, 170, 270) is inflated to hold the splittable occlusion balloon sheath (10, 100, 200) in place in the coronary sinus. The inflation of the occlusion balloon (70, 170, 270) also assists in placing the distal tip (24, 110, 210) of the splittable occlusion balloon sheath (10, 100, 200) at the center of the channel in the coronary sinus. Once the occlusion balloon (70, 170, 270) is inflated, in a preferred embodiment, a contrast medium is introduced through a lumen (34) in the splittable occlusion balloon sheath (10, 100, 200) under pressure and out the distal tip (24, 110, 210) of the splittable occlusion balloon sheath (10, 100, 200) into the coronary sinus. By injecting this medium into the coronary sinus, the vessels associated with the coronary sinus and the coronary sinus become engorged with the contrast medium and blood, allowing for a better medical viewing of those vessels. The physician can then better visualize the vessels to decide the depth and placement of the treating medical devices to be introduced by the splittable occlusion balloon sheath (10, 100, 200) into the coronary sinus, such as a temporary or permanent pacemaker lead.

Once the review of the coronary sinus has been completed, the occlusion balloon (70, 170, 270) may be deflated and the medical device to be placed in the patient's heart is then advanced through the lumen (34) of the splittable occlusion balloon sheath (10, 100, 200) into the coronary sinus. For example, a temporary or permanent pacemaker lead may be advanced through the lumen (24) of the splittable occlusion balloon sheath (10, 100, 200) to be placed within the coronary sinus or the vessels associated with the coronary sinus. A stylet may be inserted into the lumen of the pacemaker lead to provide additional stiffness for the pacemaker lead and to allow easy advancement of the pacemaker lead through the lumen of the splittable occlusion balloon sheath (10, 100, 200). Once the pacemaker lead has been advanced into the coronary sinus, the stylet is preferably removed. The pacemaker lead is then secured in place by conventional procedures. Alternatively, the occlusion balloon (70) can be reinflated after the pacemaker lead is contained within the lumen (34) within the splittable occlusion balloon sheath (100). The coronary sinus then again is engorged with blood and/or a contrast medium to assist in the placement of the pacemaker lead within the coronary sinus.

In a preferred embodiment the splittable occlusion balloon sheath (10) contains a splittable hemostasis valve through which the pacemaker lead with stylet is passed. In a more preferred embodiment the partitioned hemostasis valve system (300) disclosed in Ser. No. 09/207,295 filed Dec. 8, 1998 is secured onto the handle (20) of the splittable occlusion balloon sheath (10, 100, 200). It may be attached at any time during the medical procedure, before or after the pacemaker lead is advanced within the splittable occlusion balloon sheath (10, 100, 200). Once the pacemaker lead has been placed at the appropriate location, the partitioned hemostasis valve system (300) can be opened to remove it from the operating theater. If a conventional splittable hemostasis valve is utilized, it is split and removed from the operating theater at the same time as the splittable occlusion balloon sheath (10, 100, 200) is split and removed from the system.

Figure 3A:
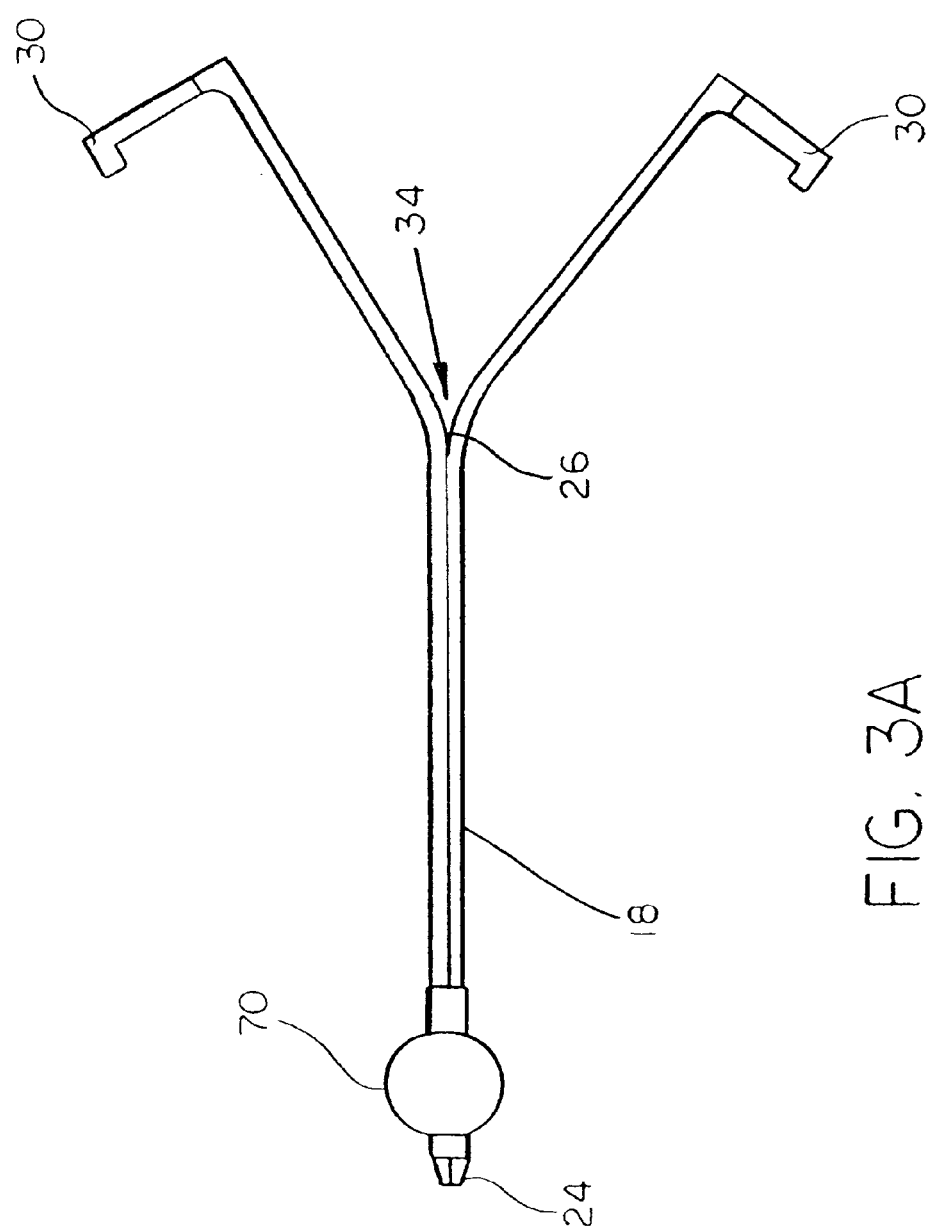
FIG. 3a is a side view of the splittable occlusion balloon sheath of FIG. 3 partially split.
Figure 13A:
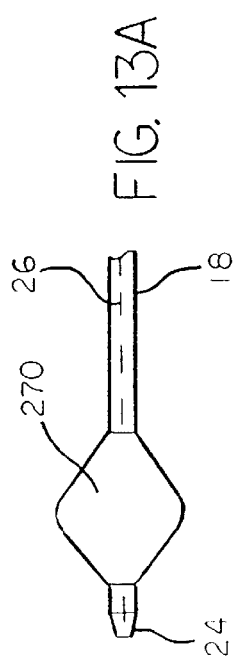
FIG. 13a is a side cutaway view of the distal portion of the splittable occlusion balloon sheath showing the use of a single side-mounted concentric occlusion balloon.
Figure 13B:
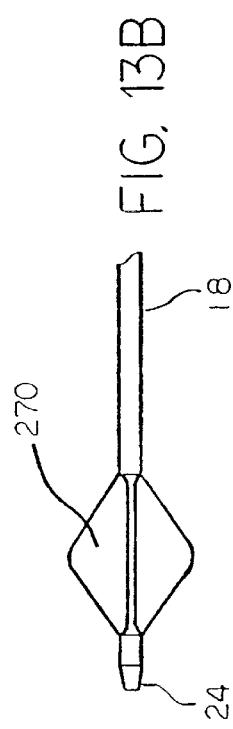
Figure 13C:
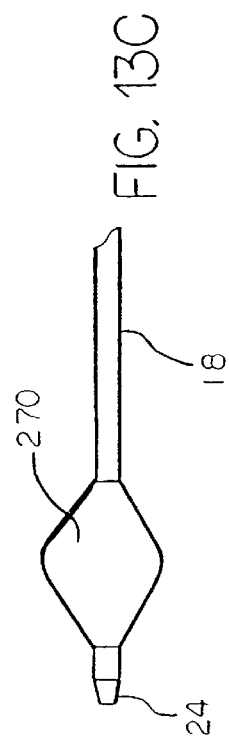
Figure 14D:
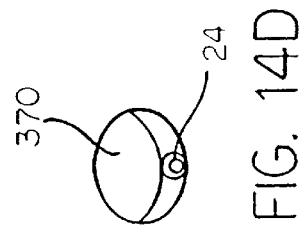
Figure 14A:
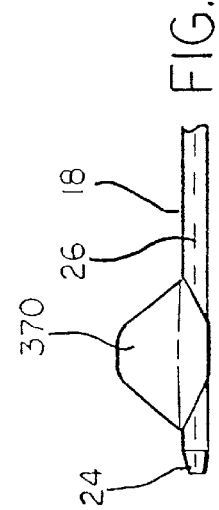
FIG. 14a is a side cutaway view of the distal portion of the splittable occlusion balloon sheath showing the use of a single side-mounted eccentric occlusion balloon.
Figure 14B:
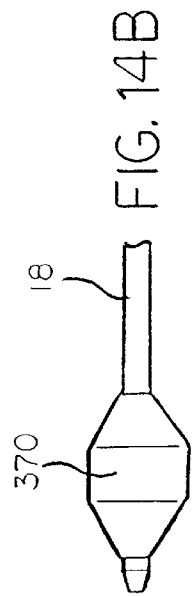
Figure 14C:
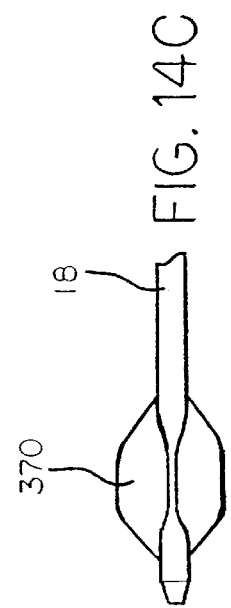

After the lead is in position, the splittable occlusion balloon sheath (10, 100, 200) is withdrawn from the body of the patient. The order of removal of stylet and splittable occlusion balloon sheath (10, 100, 200) securing the lead in place is not critical and may vary depending on the preference of the medical practitioner. Because the proximal end of the lead is generally either attached to a connector or is directly attached to the pulse generator of the pacemaker, the splittable occlusion balloon sheath (10, 100, 200) must be split into two lengthwise portions as it is removed from the patient's body as shown in FIGS. 3 and 3*a*. Once it is split, it can be removed from the operating theater. Because of the method by which the occlusion balloon (70) is secured to the splittable occlusion balloon sheath (10, 100, 200), the occlusion balloon (70) is also split into two sections, one remaining with one side of the splittable occlusion balloon sheath and the other remaining with the other side. Alternatively, if two balloons (170, 172) are utilized, one of those balloons (170) preferably remains connected to one side of the splittable occlusion balloon sheath (10, 100, 200) while the other balloon (172) remains connected to the other side of the splittable occlusion balloon sheath (10, 100, 200), as shown in FIG. 12*a*. In addition, if a single, side-mounted balloon (270) is used, as shown in FIG. 13*a*, the balloon (270) preferably remains secured to one side of the splittable occlusion balloon sheath (10, 100, 200) as the sheath is split.

The splittable occlusion balloon sheath (10, 100, 200) can be used to introduce various types of medical instruments into the body through its lumen including a permanent or temporary pacemaker lead, a defibrillator lead, ablation or sensing catheters or any such medical devices that find use if placed within the coronary sinus. These other uses are well known in the industry and are within the contemplation of the present invention.

While it is apparent from the foregoing that particular forms of the invention have been illustrated and described, various modifications can be made without departing from the spirit and scope of the invention. Accordingly, it is not intended that the invention be limited by this disclosure and all changes which come within the meaning and range of equivalence of the claims are therefore to be embraced therein.

We claim:

1. A splittable occlusion balloon sheath comprising a splittable sheath having a proximal and distal end, and an occlusion balloon secured to the splittable sheath near its distal end, wherein the occlusion balloon is splittable into separate and distinct components when the splittable sheath is split into separate sections.

2. The splittable occlusion balloon sheath of claim 1 wherein the occlusion balloon further comprises a system for separating the balloon into separate and distinct sections.

3. The splittable occlusion balloon sheath of claim 2 wherein the system for separating the occlusion balloon comprises a zone of weakness in the occlusion balloon.

4. The splittable occlusion balloon sheath of claim 3 wherein the system for separating the balloon into separate sections comprises score lines cut into the surface of the occlusion balloon.

5. The splittable occlusion balloon sheath of claim 3 wherein the system for separating the balloon into separate sections comprises zones of weakness in the balloon caused by a chemical reaction or by radiation of the occlusion balloon.

6. The splittable occlusion balloon sheath of claim 1 further comprising a splittable hemostasis valve secured within a lumen in the splittable sheath.

7. The splittable occlusion balloon sheath of claim 1 further comprising a partitioned hemostasis valve system attached to the splittable sheath.

8. The splittable occlusion balloon sheath of claim 7 wherein the partitioned hemostasis valve system comprises a partitioned hemostasis valve adaptor adapted to be secured to the splittable sheath, a housing secured to the partitioned hemostasis valve adaptor, and a partitioned hemostasis valve secured within the housing.

9. The splittable occlusion balloon sheath of claim 1 further comprising a dilator introduced into a lumen of the splittable sheath.

10. The splittable occlusion balloon sheath of claim 9 wherein the dilator comprises a precurved portion which curves through an arc from about 30 to about 120 degrees.

11. The splittable occlusion balloon sheath of claim 10 wherein the precurved portion of the dilator comprises first and second curved portions, wherein the first curved portion is curved in an arc of about 10 to about 60 degrees and wherein the second curved portion is curved in an arc of about 20 to about 90 degrees.

12. The splittable occlusion balloon sheath of claim 11 wherein the first and second portions are substantially coplanar.

13. The splittable occlusion balloon sheath of claim 10 wherein the precurved portion of the dilator comprises a first curved portion with a first arc and a second curved portion with the second arc, wherein the sum of the arcs of the first and second curved portions is about 30 to about 120 degrees.

14. The splittable occlusion balloon sheath of claim 10 wherein the precurved portion of the dilator comprises a first curved portion with a first arc and a second curved portion with the second arc wherein the sum of the arcs of the first and second curved portions is about 45 to about 90 degrees.

15. The splittable occlusion balloon sheath of claim 13 wherein the first and second curved portions are substantially coplanar.

16. The splittable occlusion balloon sheath of claim 1 wherein the splittable sheath is precurved.

17. The splittable occlusion balloon sheath of claim 16 wherein the splittable sheath comprises a curved portion curving through an arc of about 30 to about 120 degrees.

18. The splittable occlusion balloon sheath of claim 1 wherein the occlusion balloon is secured to the distal end of the splittable sheath and wherein the occlusion balloon upon inflation is generally concentric in shape around the splittable sheath.

19. The splittable occlusion balloon sheath of claim 18 wherein upon inflation of the balloon, the concentric occlusion balloon substantially circumscribes the splittable sheath.

20. The splittable occlusion balloon sheath of claim 1 wherein the occlusion balloon is secured to the distal end of the splittable sheath and wherein the occlusion balloon upon inflation is generally eccentric in shape around the splittable sheath.

21. The splittable occlusion balloon sheath of claim 20 wherein when the eccentric balloon is inflated, it circumscribes less than about 270 degrees around the splittable sheath.

22. The splittable occlusion balloon sheath of claim 1 further comprising a pair of lumen running from the proximal end to or near the distal end of the splittable sheath, wherein one of said lumen is in communication with the occlusion balloon and the second lumen is designed for introducing medical devices through the splittable sheath.

23. The splittable occlusion balloon sheath of claim 1 further comprising a lumen passing from the proximal to the distal end of the splittable sheath for the introduction of a medium through the introducer sheath and out the distal end of the splittable sheath.

24. The splittable occlusion balloon sheath of claim 1 wherein the composition of the splittable sheath and the occlusion balloons are compatible.

25. The splittable occlusion balloon sheath of claim 24 wherein both the splittable sheath and the occlusion balloon are constituted of polyethylene.

26. The splittable occlusion balloon sheath of claim 1 further comprising a system secured to an outside surface of the occlusion balloon to enhance frictional contact of the occlusion balloon with a surface of a vessel within a human.

27. The splittable occlusion balloon sheath of claim 1 wherein the occlusion balloon is secured to the splittable sheath at a location which corresponds with weakened sections in the splittable sheath useful for splitting the splittable sheath into sections.

28. The splittable occlusion balloon sheath of claim 27 wherein separate occlusion balloons are secured to the splittable sheath at separate locations, which locations correspond to sections of the splittable sheath which are weakened.

29. A splittable occlusion balloon sheath system comprising a splittable sheath having a proximal and distal ends, an occlusion balloon secured to the splittable sheath near the distal end of the splittable sheath and a precurved dilator placed within a lumen of the splittable sheath, wherein the occlusion balloon is splittable into separate and distinct components when the splittable sheath is split into separate sections.

30. The splittable occlusion balloon sheath system of claim 19 further comprising a splittable hemostasis valve attached to the splittable sheath.

31. The splittable occlusion balloon sheath system of claim 29 further comprising a partitioned hemostasis valve system attached to the splittable sheath.

32. The splittable occlusion balloon sheath system of claim 31 wherein the partitioned hemostasis valve system comprises a partitioned hemostasis valve adaptor adapted to be secured to the splittable sheath, a housing secured to the partitioned hemostasis valve adaptor, and a partitioned hemostasis valve secured within the housing.

33. A splittable occlusion balloon sheath system comprising a splittable sheath having proximal and distal ends, an occlusion balloon secured to the splittable sheath near the distal end of the splittable sheath, and a partitioned hemostasis valve system attached to the splittable sheath, wherein the occlusion balloon is splittable into separate and distinct components when the splittable sheath is split into separate sections.

34. The splittable hemostasis valve system of claim 33 wherein the partitioned hemostasis valve system comprises a partitioned hemostasis valve adaptor adapted to be secured to the splittable sheath, a housing secured to the partitioned hemostasis valve adaptor, and a partitioned hemostasis valve secured within the housing.

35. A splittable occlusion balloon sheath comprising a splittable sheath having a proximal and distal end, and an occlusion balloon secured to the splittable sheath near its distal end, wherein the occlusion balloon comprises a plurality of balloon components, each of the components secured to the splittable sheath near the distal end of the splittable introducer sheath wherein the components of the occlusion balloon are splittable into separate and distinct when the splittable sheath is split into separate sections.

* * * * *

UNITED STATES PATENT AND TRADEMARK OFFICE
CERTIFICATE OF CORRECTION

PATENT NO. : 6,758,854 B1 Page 1 of 1
DATED : July 6, 2004
INVENTOR(S) : William Butler et al.

It is certified that error appears in the above-identified patent and that said Letters Patent is hereby corrected as shown below:

Title page,
Item [63], Related U.S. Application Data, delete the following:
"Continuation-in-part of application No. 09/207,295, filed on Dec. 8, 1998, now Pat. No. 6,083,207, and a continuation-in-part of application No. 08/853,631, filed on May 9, 1997, now Pat. No. 6,277,107."

Column 1,
Line 3, delete the following,
    "CROSS-REFERENCE TO RELATED APPLICATIONS This application is a continuation-in-part application of Ser. No. 08/853,631, filed May 9, 1997 now patent No. 6,277,107, and a continuation-in-part application of Ser. No. 09/207,295 filed Dec. 8, 1998 now U.S. Pat. No. 6,083,207."

Signed and Sealed this

Second Day of November, 2004

JON W. DUDAS
*Director of the United States Patent and Trademark Office*